(12) United States Patent
Levinson et al.

(10) Patent No.: US 11,099,177 B2
(45) Date of Patent: Aug. 24, 2021

(54) PROTEIN KINASE ALLOSTERY SENSOR AND METHODS OF MAKING AND USING SAME

(71) Applicant: REGENTS OF THE UNIVERSITY OF MINNESOTA, Minneapolis, MN (US)

(72) Inventors: Nicholas Mark Levinson, Minneapolis, MN (US); Emily Ruff, Winona, MN (US); Joseph M. Muretta, Minneapolis, MN (US); David D. Thomas, Minneapolis, MN (US); Eric Lake, Minneapolis, MN (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 108 days.

(21) Appl. No.: 16/331,335

(22) PCT Filed: Sep. 8, 2017

(86) PCT No.: PCT/US2017/050608
§ 371 (c)(1),
(2) Date: Mar. 7, 2019

(87) PCT Pub. No.: WO2018/049112
PCT Pub. Date: Mar. 15, 2018

(65) Prior Publication Data
US 2019/0361014 A1 Nov. 28, 2019

Related U.S. Application Data

(60) Provisional application No. 62/385,555, filed on Sep. 9, 2016.

(51) Int. Cl.
| | | |
|---|---|---|
| *G01N 33/542* | (2006.01) | |
| *C12Q 1/48* | (2006.01) | |
| *G01N 21/64* | (2006.01) | |

(52) U.S. Cl.
CPC .......... *G01N 33/542* (2013.01); *C12Q 1/485* (2013.01); *G01N 21/6428* (2013.01); *C12Y 207/11001* (2013.01); *G01N 2021/6439* (2013.01)

(58) Field of Classification Search
CPC .................................................. C12Q 1/485
See application file for complete search history.

(56) References Cited

U.S. PATENT DOCUMENTS

| | | | |
|---|---|---|---|
| 2006/0275822 A1 | 12/2006 | Miyawaki et al. | |
| 2012/0107836 A1 | 5/2012 | Rauh et al. | |
| 2015/0204847 A1 | 7/2015 | Thomas et al. | |

OTHER PUBLICATIONS

Ohashi et al., Chem. Pharm. Bull., 2014, 62(10):1019-1025.*
Agafonov et al., Structural dynamics of the myosin relay helix by time-resolved EPR and FRET. *Proc Natl Acad Sci U S A* 106, 21625-21630 (2009).
Bayliss et al., Structural basis of Aurora-A activation by TPX2 at the mitotic spindle. *Mol Cell* 12, 851-862 (2003).
Burgess et al., The structure of C290A:C393A Aurora A provides structural insights into kinase regulation. *Acta Crystallogr F Struct Biol Commun* 71, 315-319 (2015).
Calleja et al., Monitoring conformational changes of proteins in cells by fluorescence lifetime imaging microscopy. *Biochem J* 372, 33-40 (2003).
Carmena et al., Making the Auroras glow: regulation of Aurora A and B kinase function by interacting proteins. *Curr Opin Cell Biol* 21, 796-805 (2009).
Chatterjee et al., A versatile platform for single- and multiple-unnatural amino acid mutagenesis in *Escherichia coli*. *Biochemistry* 52, 1828-1837 (2013).
Cornea et al., High-throughput FRET assay yields allosteric SERCA activators. *J Biomol Screen* 18, 97-107 (2013).
Cyphers et al., A water-mediated allosteric network governs activation of Aurora kinase A. *Nat Chem Biol* 13, 402-408 (2017).
D'Assoro et al., Aurora-A Kinase as a Promising Therapeutic Target in Cancer. *Front Oncol* 5, 295 (2015).
Dodson et al., Activation of Aurora-A kinase by protein partner binding and phosphorylation are independent and synergistic. *J Biol Chem* 287, 1150-1157 (2012).
Gerrits et al., Cell-Free Synthesis of Defined Protein Conjugates by Site-Directed Cotranslational Labeling, 2013, *Madam Curie Bioscience Database*. Landes Bioscience; Retrieved from the Internet: www.ncbi.nih.gov/books/NBK6497.
Gruber et al., Discovery of enzyme modulators via high-throughput time-resolved FRET in living cells. *J Biomol Screen* 19, 215-222 (2014).
Hirota et al., Aurora-A and an interacting activator, the LIM protein Ajuba, are required for mitotic commitment in human cells. *Cell* 114, 585-598 (2003).
Huse et al., The conformational plasticity of protein kinases. *Cell* 109, 275-282 (2002).
Kufer et al., Human TPX2 is required for targeting Aurora-A kinase to the spindle. *J Cell Biol* 158, 617-623 (2002).
Levinson et al., Structural basis for the recognition of c-Src by its inactivator Csk. *Cell* 134, 124-134 (2008).
Levinson, Nicholas "Kinome-Wide Spectroscopic Study of Drug Binding Site Electrostatics," Grant Abstract, Grant No. GM102288 [online]. National Institutes of Health, project dates Aug. 13, 2012 to Nov. 30, 2017 [retrieved on Nov. 10, 2020]. 2 pgs.
Levinson, Nicholas "A Novel Time-Resolved Fluorescence-Based High-Throughput Screening Technology for Discovering Allosteric Kinase Inhibitors," Grant Abstract, Grant No. CA217695 [online]. National Institutes of Health, project dates Aug. 1, 2017 to Jul. 31, 2020 [retrieved from the internet on Nov. 10, 2020]. 2 pgs.

(Continued)

*Primary Examiner* — Bin Shen
(74) *Attorney, Agent, or Firm* — Mueting Raasch Group

(57) ABSTRACT

A protein kinase that includes a donor molecule and an acceptor molecule, methods of making the protein kinase, and methods of using the protein kinase are described. Measurement of the conformation of the kinase can be obtained using intramolecular FRET. The protein kinase can be used to, for example, identify conformational changes involved in kinase regulation, that is, as an allostery sensor; to identify kinase-binding molecules including, for example, kinase inhibitors; to identify cancer therapeutics; or for high-throughput screening.

9 Claims, 18 Drawing Sheets

(56) References Cited

OTHER PUBLICATIONS

Lu et al., Prolyl cis-trans isomerization as a molecular timer. *Nat Chem Biol* 3, 619-629 (2007).
Macurek et al., Polo-like kinase-1 is activated by aurora A to promote checkpoint recovery. *Nature* 455, 119-123 (2008).
Martin et al., A novel mechanism by which small molecule inhibitors induce the DFG flip in Aurora A. *ACS Chem Biol* 7, 698-706 (2012).
Muretta et al., High-performance time-resolved fluorescence by direct waveform recording. *Rev Sci Instrum* 81, 103101 (2010).
Muretta et al., Direct real-time detection of the structural and biochemical events in the myosin power stroke. *Proc Natl Acad Sci U S A* 112, 14272-14277 (2015).
Petersen et al., Fluorescence lifetime plate reader: resolution and precision meet high-throughput. *Rev Sci Instrum* 85, 113101 (2014).
Rowan et al., Insights into Aurora-A kinase activation using unnatural amino acids incorporated by chemical modification. *ACS Chem Biol* 8, 2184-2191 (2013).
Ruff, "Development of Kinase Allostery FRET Assays for Mechanistic Studies and Drug Design," Pharmacology Department Retreat (University of Minnesota). Sep. 11, 2015. 33 pgs.
Ruff et al., "Novel Kinase Allostery FRET Assays for Mechanistic Studies and Drug Design," Annual Departmental Retreat (Department of Pharmacology, University of Minnesota). Jan. 29, 2016. 1pg.
Satinover et al., Activation of Aurora-A kinase by protein phosphatase inhibitor-2, a bifunctional signaling protein. *Proc Natl Acad Sci U S A* 101, 8625-8630 (2004).
Schaaf et al., High-Throughput Spectral and Lifetime-Based FrRET Screening in Living Cells to Identify Small-Molecule Effectors of SERCA. *SLAS Discov* 22, 262-273 (2017).
Schaap et al., Development of a steady-state FRET-based assay to identify inhibitors of the Keapl-NRF2 protein-protein interaction. *Protein Sci* 22, 1812-1819 (2013).
Schindler et al., Structural mechanism for STI-571 inhibition of abelson tyrosine kinase. *Science* 289, 1938-1942 (2000).
Sessa et al., Mechanism of Aurora B activation by INCENP and inhibition by hesperadin. *Mol Cell* 18, 379-391 (2005).
Trivedi et al., Direct measurements of the coordination of lever arm swing and the catalytic cycle in myosin V. *Proc Natl Acad Sci U S A* 112, 14593-14598 (2015).
Zhao et al., Modulation of kinase-inhibitor interactions by auxiliary protein binding: crystallography studies on Aurora A interactions with VX-680 and with TPX2. *Protein Sci* 17, 1791-1797 (2008).
Zorba et al., Molecular mechanism of Aurora A kinase autophosphorylation and its allosteric activation by TPX2. *Elife* 3, e02667 (2014).
PCT/US17/50608 filed Sep. 8, 2017, International Search Report and Written Opinion dated Nov. 3, 2017. 12 pgs.
PCT/US17/50608 filed Sep. 8, 2017, International Preliminary Report on Patentabilty, dated Mar. 21, 2019. 16 pgs.

* cited by examiner

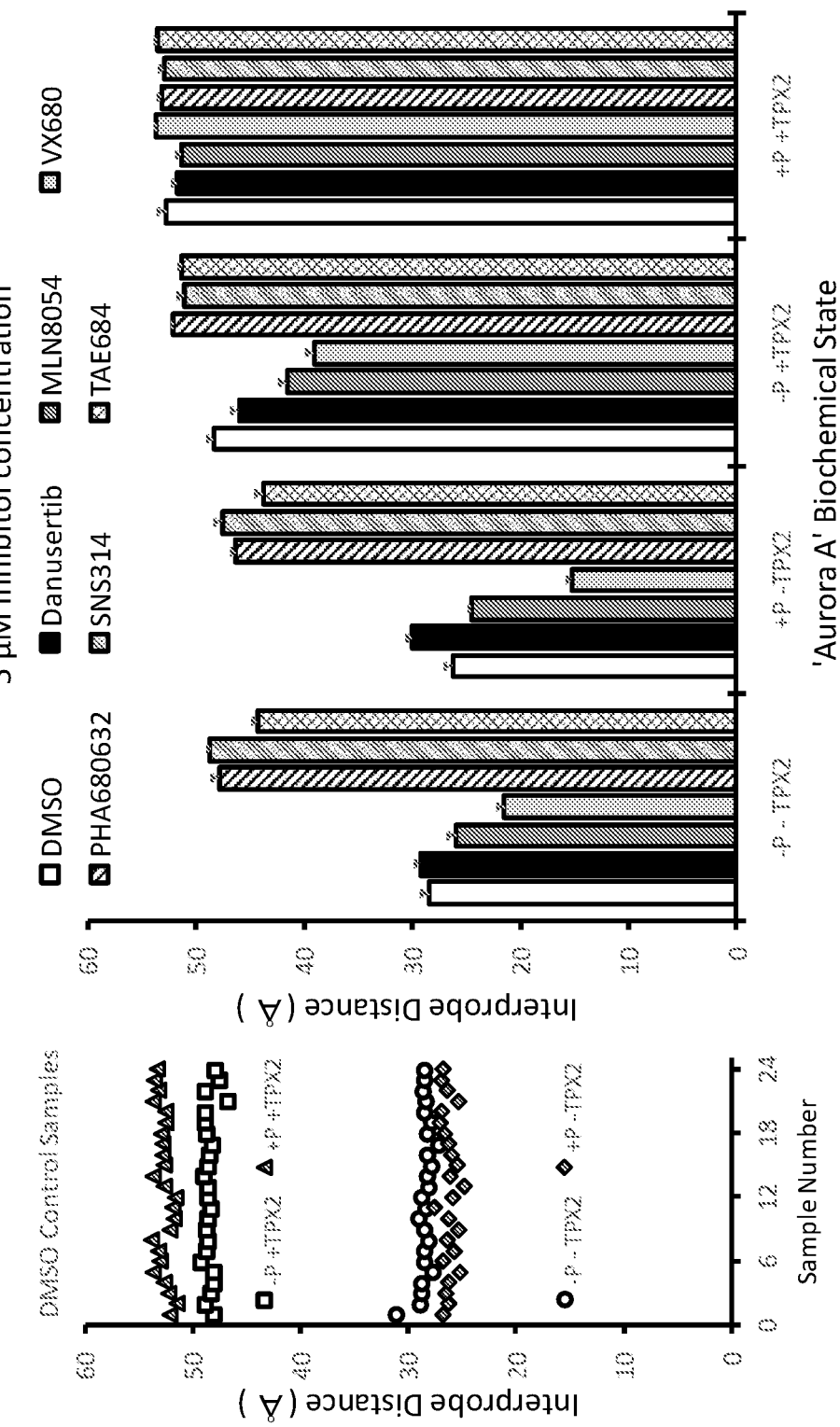

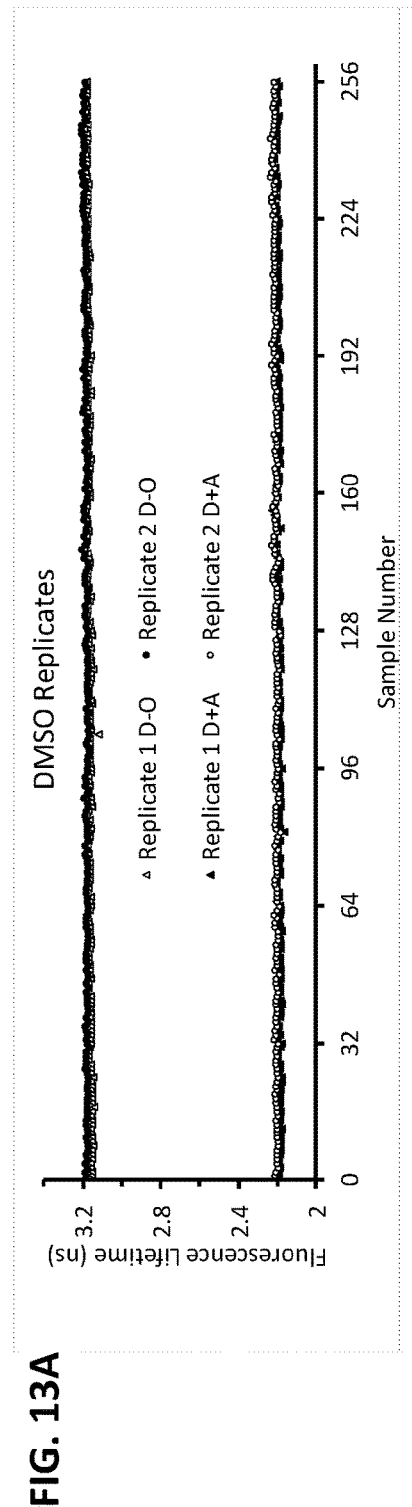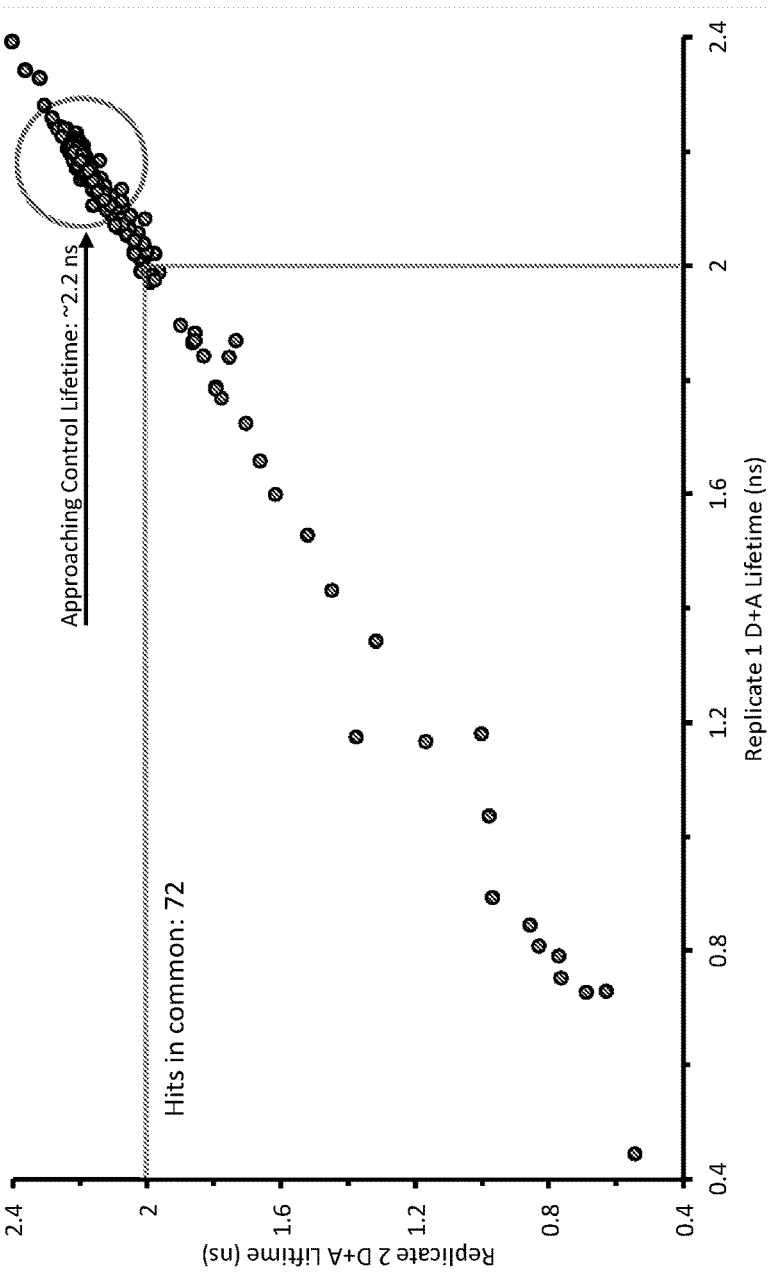
FIG. 13A
FIG. 13B

PROTEIN KINASE ALLOSTERY SENSOR AND METHODS OF MAKING AND USING SAME

CONTINUING APPLICATION DATA

This application is the § 371 U.S. National Stage of International Application No. PCT/US2017/050608, filed Sep. 8, 2017, which claims the benefit of U.S. Provisional Application Ser. No. 62/385,555, filed Sep. 9, 2016, the disclosures of each of which are incorporated by reference herein.

GOVERNMENT FUNDING

This invention was made with government support under GM102288-03 and CA217695-01 awarded by National Institutes of Health. The government has certain rights in the invention.

BACKGROUND

Many human cancers feature deregulation of kinase signaling, and small molecule kinase inhibitors form a major class of anticancer drugs. Most currently available inhibitors target the highly conserved ATP-binding site, however, and are, therefore, limited in selectivity due to the structural homology that all kinases share in their ATP-binding site. Non-selective off-target binding can cause toxicity and debilitating side effects, thus there is a substantial clinical need to develop kinase inhibitors that are highly specific for individual kinases. Additionally, clinical resistance is seen to many kinase inhibitors, typically within one year. Thus, there is a sustained need for additional kinase inhibitors and for methods of identifying such inhibitors.

SUMMARY OF THE INVENTION

Protein kinases are major drug targets in oncology, but most existing inhibitors are ATP-competitive (orthosteric) and poorly selective for specific kinases. A promising approach to developing highly selective kinase inhibitors is to identify small molecules that bind to allosteric sites on kinases and modulate the allosteric mechanisms intrinsic to all kinases. However, no robust assay technology currently exists that can directly identify allosteric kinase inhibitors and distinguish them from orthosteric inhibitors.

This disclosure describes an engineered protein kinase (also referred to herein as a "kinase") and methods of making and using the kinase that can be used to directly monitor allosteric structural changes in any kinase domain, from any kinase, upon ligand binding, based on intramolecular distance measurements made by Forster resonance energy transfer (FRET). In some embodiments, the methods include measuring the conformation of a kinase including, for example, the position of the kinase activation loop, an important allosteric structural element modulated by intrinsic regulatory mechanisms and by certain kinase inhibitors. Measurement of the proportion of a kinase in a particular conformation can allow discrimination of the effects of different subtypes of allosteric inhibitors and can provide direct information on the nature of the induced structural change. The described methods can in some embodiments be used to accelerate allosteric kinase inhibitor discovery.

In one aspect, this disclosure describes a protein kinase that includes a donor molecule and an acceptor molecule. The protein kinase can exist in at least a first conformation and a second conformation; when the kinase exists in the first conformation, energy is transferred from the donor molecule to the acceptor molecule with higher efficiency than when the kinase exists in the second conformation.

In another aspect, this disclosure describes methods of making the protein kinases described herein. For example, this disclosure describes covalently linking a protein kinase to a donor molecule and an acceptor molecule.

In a further aspect, this disclosure describes a method including providing a protein kinase comprising a donor molecule and an acceptor molecule. The protein kinase can exist in at least a first conformation and a second conformation; in the first conformation, energy is transferred from the donor molecule to the acceptor molecule; and, in the second conformation, the efficiency with which energy is transferred from the donor molecule to the acceptor molecule differs from the efficiency with which energy is transferred from the donor molecule to the acceptor molecule in the first conformation. The method further includes measuring the proportion of protein kinase in the first conformation. In some embodiments, the method can include contacting the protein kinase with a small molecule and determining the proportion of protein kinase in the first conformation when the small molecule is in contact with the kinase. In some embodiments, these methods can be used to, for example, screen for small molecules that modulate a conformation change in the kinase.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 2(A-C) shows validation of AurA FRET-labeled samples.

FIG. 3(A-D) shows representative FRET titration data with increasing ADP concentration (0 millimolar (mM); 1.7 mM; 5 mM; 15 mM; 45 mM; and 135 mM).

FIG. 4(A-B) shows a comparison of crystal structures and steady-state FRET data for two inhibitors that induce conformational changes in AurA. Structure figures were made using PyMOL. DFG aspartate, activation loop (black), and inhibitors are indicated.

FIG. 5(A-B) shows an exemplary high-throughput screen performed using high-throughput nanosecond time-resolved fluorescence measured by direct waveform recording or steady-state fluorescence emission measured by spectral recording.

FIG. 6(A-C) shows the analysis of a LOPAC library screen using high-throughput time-resolved fluorescence detection.

FIG. 8(A-C) shows representative DMSO control waveforms along with the numerical fits to the waveforms. The residuals from the fits are shown in the bottom panels. Direct fluorescence waveforms of donor-only labeled and donor+acceptor labeled samples were individually recorded using a custom-built instrument designed by Fluorescence Innovations, as further described in Example 3.

FIG. 9(A-C) shows exemplary DMSO control sample distance determinations for four different biochemical states of AurA (with and without phosphorylation, and with and without Tpx2).

FIG. 10(A-B) shows exemplary FRET-based measurements of AurA conformation in the presence of 6 AurA kinase inhibitors. Time-resolved fluorescence was measured in 384-well plates for each of the four biochemical states of AurA (with and without phosphorylation, with and without Tpx2) in the presence of saturating concentrations (5 μM) of each of the 6 inhibitors (VX-680, MLN-8054, TAE-684, SNS-314, Danusertib, and PHA-680632). There were 4 replicates of each inhibitor for each biochemical state. 24 control samples with zero inhibitor concentration were fit simultaneously with the samples containing inhibitors using global analysis (several fitting parameters are shared globally among all datasets), providing internal references for the distances observed in the presence of inhibitors. FIG. 10A. Distances determined for the 24 DMSO control samples are shown, demonstrating consistency with the original 96 DMSO control samples from FIG. 9, which were fit independently. FIG. 10B. Distances determined for each of the 6 inhibitors bound to each of the four biochemical forms of AurA are shown. Values are the mean and standard deviations calculated from the four replicates. The results show that three of the compounds (danusertib, MLN8054, VX680, solid bars) bind to the DFG-Out state of AurA in the absence of Tpx2 (−P−Tpx2 and +P−Tpx2), yielding short FRET distances on the order of 30 Å. In contrast, the other three compounds (PHA680632, SNS314, and TAE684) yielded long distances under these conditions, indicating that these compounds induce the DFG-In state when they bind to AurA. Strikingly, in the presence of saturating Tpx2 (10 μM, −P+Tpx2, +P+Tpx2), all 6 inhibitors yield long distances indicative of adoption of the active DFG-In state of AurA. These data indicate that any conformational preferences of the compounds for the DFG-Out state of AurA are sufficiently small to be overcome by the effects of Tpx2.

FIG. 12(A-C) shows a comparison between the distance determinations obtained using two different sets of labeling sites on AurA. For the second set, the cysteine labeling site at position L225 on the αD helix of AurA was moved downstream to position K227, and distances were measured for unphosphorylated AurA without Tpx2 bound to the same 6 inhibitors described above.

FIG. 13(A-B) shows the results of two replicate screens of the Library of Pharmacologically Active Compounds (LOPAC). 50 nanomolar (nM) AurA biosensor (without Tpx2) was run in duplicate against the LOPAC library in 1536-well plate format. Waveforms were fit to a single exponential model of decay by using the least-squares minimization global analysis to determine an average fluorescence lifetime. 256 DMSO replicates were present in each of the screened plates. FIG. 13A. A plot of the donor-only (D−O) and donor+acceptor (D+A) lifetimes demonstrated the consistency of the lifetime measurements. FIG. 13B. Plotting the donor+acceptor lifetimes of the two replicate plates revealed a high degree of consistency between the two screens and further demonstrates the robustness of these data. The majority of compounds clustered around an average lifetime of approximately 2.2 nanoseconds (ns) consistent with the DMSO controls, while the majority of hits, as defined by a 5 SD change in lifetime about the mean of the controls, fell below 2.0 ns (see gray lines). Fluorescent compounds were detected using a spectral similarity index in which false positives are ruled out by 3 SD of the mean of controls. 72 hits were identified in common between the replicate screens.

DETAILED DESCRIPTION

Figure 1:
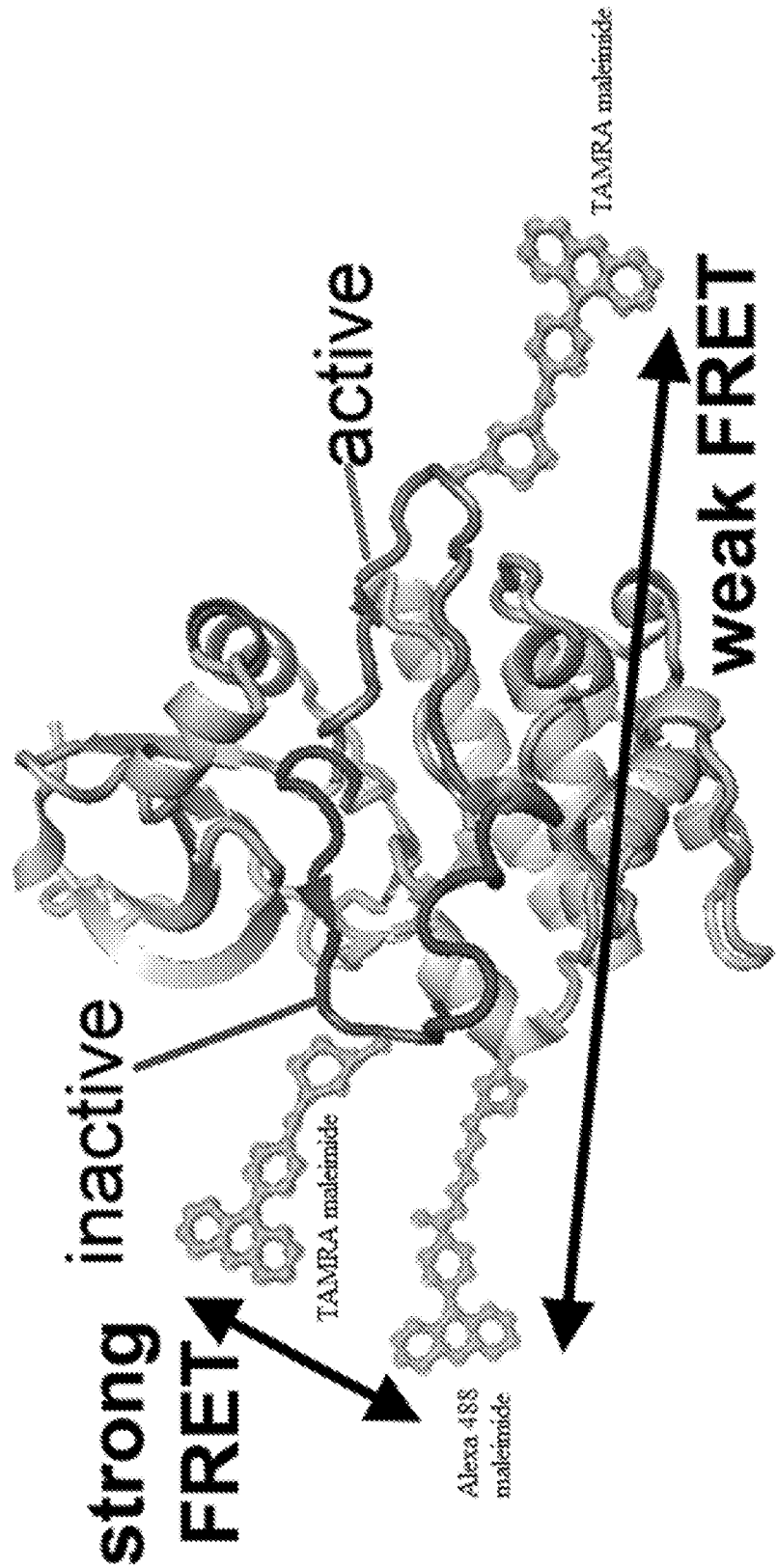
FIG. 1 shows a model of Förster resonance energy transfer (FRET)-labeled Aurora A (AurA) built in PyMOL using Protein Data Bank (PDB) ID 3UNZ (inactive) and IOL5 (active). Modeled fluorophores are TAMRA maleimide and Alexa 488 maleimide.

This disclosure describes a kinase and methods of making and using the kinase that can be used to directly monitor structural changes in the kinase upon ligand binding using intramolecular Förster resonance energy transfer (FRET). In some embodiments, measurement of the conformation of a kinase including, for example, the position of the kinase activation loop, using intramolecular FRET can allow discrimination of the effects of different allosteric kinase inhibitors and can provide direct information on the nature of the induced structural change, accelerating allosteric kinase inhibitor discovery.

Signal transduction by protein kinases controls many aspects of cell development and proliferation. The phosphorylation activity of kinases is therefore tightly regulated, and deregulation by mutation or overexpression of kinases and their cofactors has been linked to many cancers. In general, kinase regulation is focused on the transition between active and auto-inhibited (inactive) states. For each kinase, there is a unique set of mediators of this transition, including phosphorylation and protein and small molecule ligands. The active and auto-inhibited states are distinguished mainly by the conformations of two features: helix C, which forms one side of the active site and contains a conserved catalytic Glu residue; and the activation loop, which forms part of the substrate peptide docking site and contains a conserved catalytic Asp. Comparison of crystal structures of active and auto-inhibited kinase conformations suggests that in the process of activation, residues of the activation loop move nanometer-scale distances, unblocking the substrate binding site and positioning the active site for catalysis. The structural dynamics of the activation loop are, therefore, often a key determinant of kinase activity. Little is known, however, about how the structure of the activation loop changes during allosteric activation, and how these conformational changes coordinate function. One reason for this lack of understanding is that, at the time of the invention, no real-time assays were available to study the structural state and dynamics of the kinase activation loop. In some embodiments, this disclosure describes an assay for activation loop conformation that enables the mechanistic study of allosteric activation and allosteric inhibition, and improves on current high-throughput screening (HTS) methods, allowing for the discovery of next-generation small molecule kinase inhibitors for treatment of cancer.

In one aspect, this disclosure describes an assay for determining the conformational rearrangement of a kinase. In some embodiments, the conformational rearrangement is of the activation loop of the kinase. In some embodiments, the kinase is a clinically relevant kinase including for example, the kinase Aurora A (AurA), a key regulator of mitosis that has been identified as an oncogene and that has generated interest as a chemotherapeutic drug target. Förster resonance energy transfer (FRET) can be used to make nanometer-scale distance measurements of the conformational rearrangement. During FRET, an excited fluorophore (the donor, "D") transfers energy non-radiatively to an acceptor fluorophore ("A"). The efficiency of this transfer, E, is determined by the equation $E=1/(1+r/R_0)^6$, where r is the distance between the fluorophores and $R_0$ is the Förster distance for the D and A pair (approximately 1 nanometer (nm)–10 nm), determined by the quantum yield of D and the fluorophores' spectral overlap). FRET is thus highly sensitive to nanometer-scale changes in the distance between D and A.

In some embodiments, site-directed mutagenesis and/or chemical labeling can be used to introduce two distinct fluorophores into the same kinase molecule, and steady-state (SS) and/or time-resolved (TR) FRET can be used to measure changes in the conformation(s) of the kinase. The FRET assay can be used to determine kinase conformational dynamics. In addition, site-directed mutagenesis can be used to investigate residues and regions of the kinase which are important in determining its unique set of regulatory mechanisms. FRET can be used to determine the allosteric modulation of a kinase (including, for example, AurA) by small molecule inhibitors in solution and to perform high-throughput screens to discover new kinase inhibitor drug candidates.

Kinase Drug Targets and Aurora A

The field of cancer drug development is increasingly focused on the search for allosteric kinase inhibitors, which bind outside of the ATP binding pocket and are therefore highly specific. These drugs take advantage of allosteric mechanisms which are regulated for each kinase by a specific set of effectors, including ligands, allosteric protein-protein interactions, and post-translational modifications such as phosphorylation. Better understanding of the allostery regulating a given kinase drug target can inform the development of drugs with strong conformational preferences. However, these regulatory mechanisms remain poorly understood and difficult to target because, previous to this invention, no assay provided a direct structural readout of conformational changes in real time in solution.

The methods described herein can be used to study allosteric regulators and to identify specifically targeted allosteric drugs. While in some contexts the methods and kinases are described herein in the context of an exemplary embodiment in which the kinase is Aurora A, the kinases and methods described herein can be applied to other kinases. Exemplary other kinases include, for example, Aurora B, Plk1, Cdk2 and Cdk4, MEK, b-Raf, p38, c-Src, BCR-Abl, c-Met, EGFR, Her2, Flt3, Kit, ALK, FGFR, VEGFR, JAK1, JAK2.

Aurora A (AurA) is a key regulator of mitosis that has been identified as an oncogene and has generated interest as a chemotherapeutic drug target. Targeting specific conformations of AurA has recently been shown to be a novel strategy for treating tumor suppressor protein p53-altered liver cancer. An inhibitor known to alter the conformation of AurA, MLN8054, has been shown to disrupt a key interaction between AurA and the oncoprotein MYC, which itself has no known druggable surfaces, allowing successful treatment of this cancer in mice. Thus, targeting a specific conformation of a kinase, rather than simply the nucleotide binding site, can be important to elicit a therapeutic effect. According to X-ray structure data for AurA, residues of the activation loop move tens of angstroms in the transition between the autoinhibited and fully activated states.

AurA is activated by allosteric binding partners, including TPX2, which recruits it to the mitotic spindle, and by phosphorylation of the activation loop at T288 ("phosphoT288"). Different pools of AurA in vivo appear to be activated by different factors. For example, during mitosis, AurA bound to spindle microtubules is bound to TPX2 but is not phosphorylated, while at the poles of the cell AurA is phosphorylated but not in proximity to TPX2. For many kinases, phosphorylation of the activation loop alone confers maximal activity; the reason this is not the case for AurA is unknown.

Protein Kinases

In one aspect, this disclosure describes a protein kinase including a donor molecule and an acceptor molecule. The protein kinase can exist in at least two conformations: a first conformation and a second conformation. When the kinase is in the first conformation, energy is transferred from the donor molecule to the acceptor molecule with higher efficiency than when the kinase exists in the second conformation. This more efficient energy transfer occurs because in the first conformation the donor molecule and the acceptor molecule are closer together than in the second conformation. In some embodiments, the distance between the donor molecule and the acceptor molecule when the kinase is in the second conformation is at least 1 Angstrom (Å) greater, at least 2 Å greater, or at least 5 Å greater than the distance between the donor molecule and the acceptor molecule when the protein kinase is in the first conformation. In some embodiments, a kinase conformation can be defined as a kinase having a defined distance or range of distances between the donor molecule and the acceptor molecule. In some embodiments, distinct kinase conformations (including, for example, a first conformation, a second, conformation, a third conformation, etc.) can be defined as having a distance between the donor molecule and the acceptor molecule that differs by at least 1 Angstrom (Å), at least 2 Å greater, or at least 5 Å from the distance between donor molecule and the acceptor molecule of another conformation.

In some embodiments, the donor molecule includes a fluorophore. In some embodiments, the acceptor molecule includes a fluorophore or a dark acceptor. Any suitable fluorophore or dark acceptor may be used. For example, the fluorophore can include a molecule based on the fluorescein scaffold including, for example, AlexaFluor 488, AlexaFluor 568 or other Alexa series dyes; an Oregon Green or a Rhodamine dye; a fluorophore based on the cyanine scaffold including, for example, Cy3 or Cy5; boron-dipyrromethene (BODIPY) or a BODIPY variant; acrylodan (6-acryloyl-2-dimethylaminonaphthalene); 5-({2-[(iodoacetyl)amino]ethyl}amino)naphthalene-1-sulfonic acid (IAEDANS); a dye that can be incorporated co-translationally by nonsense suppression such as hydroxycoumarin derivatives or acridon-2-ylalanine; etc.

Energy is transferred from the donor molecule to the acceptor molecule via Förster resonance energy transfer (FRET). Although, in many embodiments, energy can transfer between the donor molecule and the acceptor molecule in both the first conformation and the second conformation (and, potentially, in additional conformations as well), the change in the distance between the donor molecule and the acceptor molecule in different conformations results in a change in the efficiency with which energy is transferred from the donor molecule to the acceptor molecule. Using FRET to measure the distance between the two molecules allows different conformations of a kinase to be distinguished; that is, the kinase can act as an allostery sensor. In addition, using FRET does not require that the kinase be phosphorylated on its activation loop, locking the loop into an active conformation. Thus, the first conformation and second conformation of the kinase can include conformations that are only adopted by a non-phosphorylated kinase. Moreover, in contrast to a method that uses a single environmentally-sensitive fluorescent probe covalently incorporated into the activation loop to measure the binding of allosteric inhibitors to kinases, the use of a kinase including both a donor molecule and an acceptor molecule allows for the measurement of the distance between the two probes, yielding more nuanced information and providing data more suitable for use in mechanistic studies. In contrast, some existing methods use a kinase with a single environmentally-sensitive fluorescent probe, but these methods provide little if any structural information.

In some embodiments, the function of the protein kinase including the donor molecule and the acceptor molecule is indistinguishable from a wild type kinase and/or a kinase that does not include the donor molecule or the acceptor molecule. For example, in some embodiments, substrate phosphorylation by the protein kinase including the donor molecule and the acceptor molecule is indistinguishable from substrate phosphorylation by the protein kinase that does not include the donor molecule or the acceptor molecule In some embodiments, at least one of the donor molecule or the acceptor molecule can bind to an ATP-binding site of the protein kinase. In some embodiments, at least one of the donor molecule or the acceptor molecule is covalently linked to the protein kinase. The donor molecule or the acceptor molecule can be covalently linked to the protein kinase by any suitable means including, for example, by means of thiol-maleimide chemistry, azide/alkyne Click chemistry, aldehyde/hydrazine chemistry, aldehyde/hydroxylamine chemistry, native chemical ligation, and/or intein-mediated protein splicing. In some embodiments, the donor molecule or the acceptor molecule can be incorporated in the protein kinase co-translationally using a nonsense suppression methodology. In some embodiments, the donor molecule or the acceptor molecule can be covalently linked to the activation loop, the alpha-C helix, the D-helix, or the phosphate binding P-loop of the kinase. In some embodiments, the donor molecule can be covalently linked to a static portion of the kinase and the acceptor molecule can be covalently linked to a non-static portion of the kinase. In some embodiments, the acceptor molecule can be covalently linked to a static portion of the kinase and the donor molecule can be covalently linked to a non-static portion of the kinase. For example, in one illustrative embodiment, the donor molecule is positioned on the activation loop of a kinase and the acceptor molecule is positioned on the D-helix of a kinase.

In some embodiments, the protein kinase is phosphorylated on, for example, the activation loop. In some embodiments, in at least one of its conformations, the protein kinase can be bound to a nucleotide, an activator protein, an activator peptide, a small-molecule allosteric modulator, or combinations thereof. In some embodiments, the kinase can include an Aurora kinase including, for example, Aurora A (AurA). Exemplary other kinases include, for example, Aurora B, Plk1, Cdk2 and Cdk4, MEK, b-Raf, p38, c-Src, BCR-Ab1, c-Met, EGFR, Her2, Flt3, Kit, ALK, FGFR, VEGFR, JAK1, JAK2.

In some embodiments, the kinase can include a mutation including, for example, a point mutation. In some embodiments, the mutation can be introduced using site-directed mutagenesis. Mutation of the kinase and/or site-directed mutagenesis may be used, for example, to study the role of an amino acid residue in the mechanism of allosteric regulation or in the mechanism of action of a small molecule inhibitor. In some embodiments, site-directed mutagenesis may also be used to introduce a resistance mutation developed by a kinase. In some embodiments, a mutation can be introduced to effect allosteric regulation of the kinase. For example, a mutation can include a mutation of the gatekeeper residue in the active site of the kinase.

Methods of Making the Protein Kinase

In another aspect, this disclosure provides methods for making the protein kinases described herein.

In some embodiments, the method includes covalently linking a protein kinase to a donor molecule and an acceptor molecule. The donor molecule or the acceptor molecule can be linked to the kinase at any suitable location. For example, the donor molecule or the acceptor molecule can be linked to a residue of the activation loop, the P-loop, the D-helix, or the C-helix of the protein kinase.

For example, for ApoA, in some embodiments, immobile mutagenesis sites on helix D (Q223C, K224C, and L225C) and/or at the kinase C-terminus (S388C, K389C) may be used. In some embodiments, activation loop mutations H280C, S283C, S284C, R285C, and T287C may be used; although mutations H280C and R285C lead to severe defects in function, and mutation S283C leads to weakened binding of activator peptide TPX2. In some embodiments, use of sites S284C and T287C may be preferred. In some embodiments, use of sites L225C and T287C may be preferred.

In some embodiments, at least one of the donor molecule or the acceptor molecule is covalently linked to the protein kinase. The donor molecule and/or the acceptor molecule can be covalently linked to the protein kinase by any suitable means including, for example, by means of thiol-maleimide chemistry, azide/alkyne Click chemistry, aldehyde/hydrazine chemistry, aldehyde/hydroxylamine chemistry, native chemical ligation, and/or intein-mediated protein splicing. In some embodiments, the donor molecule and/or the acceptor molecule can be incorporated in the protein kinase co-translationally using a nonsense suppression methodology.

In some embodiments, the protein kinase can be covalently linked to the donor molecule and/or the acceptor molecule by reacting a thiol with a maleimide, an azide with an alkyne, or an aldehyde with a hydrazine, a hydrazide, or a hydroxylamine. In some embodiments, the protein kinase can be covalently linked to the donor molecule and/or the acceptor molecule by co-translationally incorporating an amino acid. For example, the amino acid can be incorporated by nonsense suppression (e.g., Chatterjee et al. *Biochemistry*, 2013, 52(10):1828-37). In some embodiments, the amino acid being incorporated can include a donor molecule or an acceptor molecule. In some embodiments, the amino acid can include a fluorescent amino acid. In some embodiments, the amino acid being incorporated can be capable of being conjugated to a donor molecule or an acceptor molecule. In some embodiments, site-directed mutagenesis may be used to incorporate mutations into the kinase in addition to the cysteines used for labeling. These mutations may be engineered to study mechanisms of function, regulation, and/or drug resistance.

As further described in the Examples, preparation of FRET-labeled constructs, may include, in some embodiments, mutation of certain cysteine residues of the kinase to non-cystine residues (e.g., serines). In some embodiments, the selected cysteine residues of the kinase may be those residues observed to be solvent-exposed in published crystal structures. For example, for preparation of FRET-labeled AurA constructs, AurA constructs with cystines residues mutated to serine ("Cys-lite"), may include, for example, AurA C290S C393S ("AurA CL2") and AurA C290S C393S C247S ("AurA CL3").

Figure 2A:
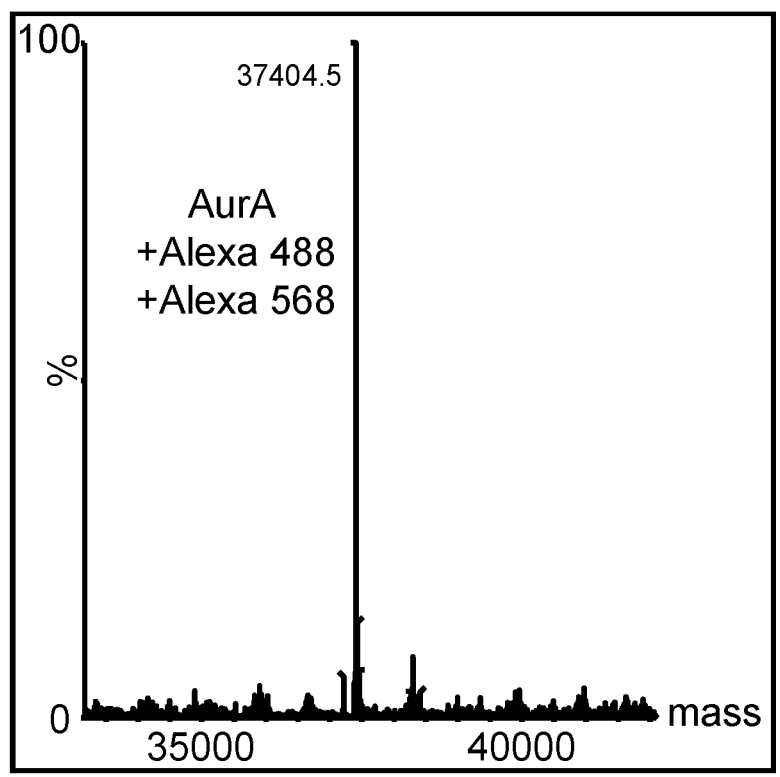
FIG. 2A. Mass spectrum confirming the incorporation of donor (Alexa 488) and acceptor (Alexa 568) fluorophores into the mutant AurA C247S C290S C393S ("AurA CL3") L225C T287C. Spectrum obtained by University of Minnesota Center for Mass Spectrometry and Proteomics.
Figure 2B:
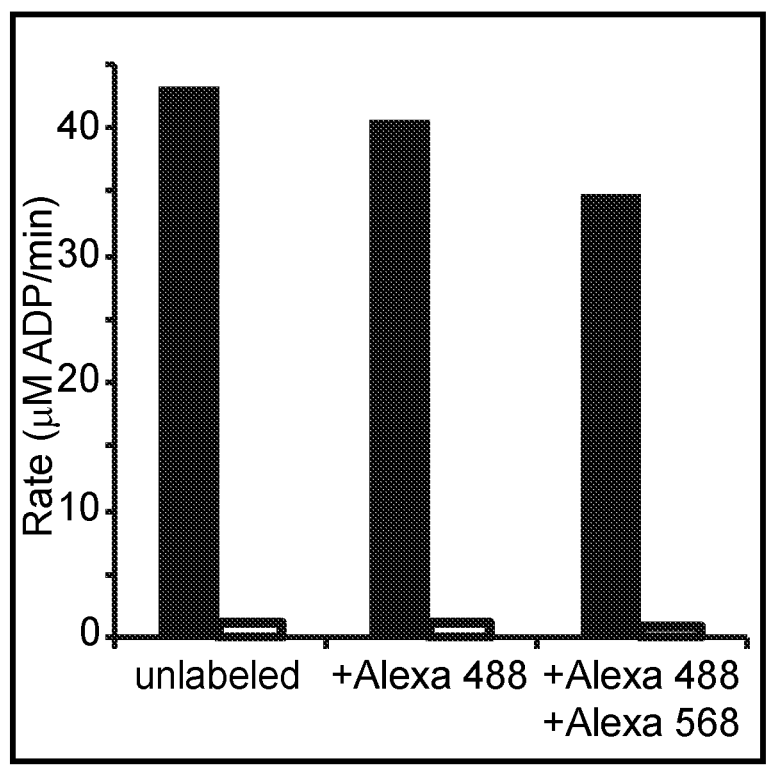
FIG. 2B. Substrate phosphorylation activity of labeled and unlabeled representative AurA construct (unphosphorylated AurA CL3 L225C T287C) in the presence (black) and absence (white) of 10 micromolar ($\mu$M) TPX2 activator.
Figure 2C:
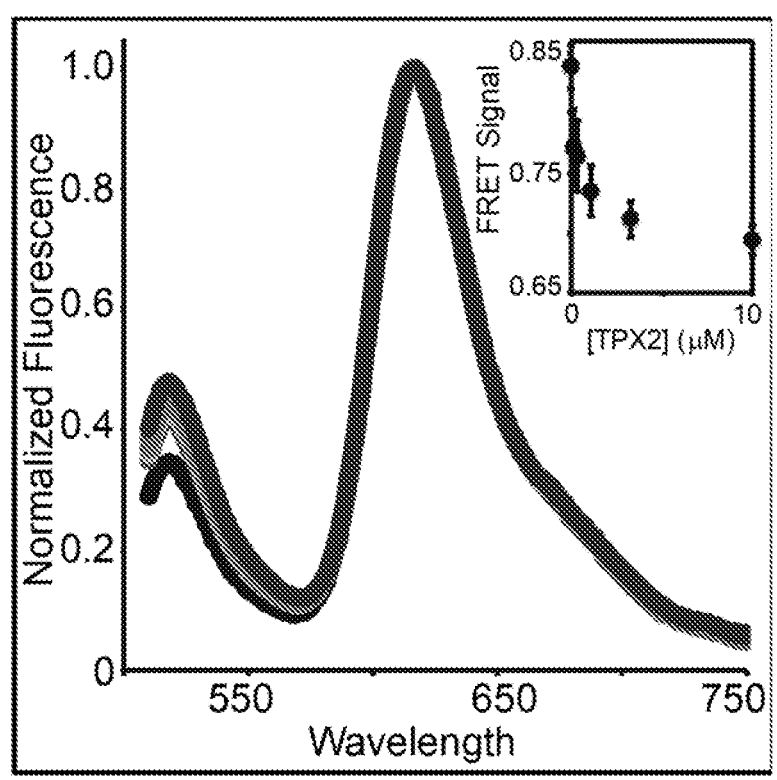
FIG. 2C. Steady-state fluorescence titration data, performed with FRET-labeled unphosphorylated AurA CL3 L225C T287C normalized to acceptor maximum. Lines show an average of two assays (including TPX2 concentrations of 0 $\mu$M; 0.1 $\mu$M; 0.3 $\mu$M; 1 $\mu$M; 3 $\mu$M; and 10 $\mu$M). Inset: calculated FRET for the spectra shown as a function of TPX2 concentration from 1 $\mu$M to 10 $\mu$M.
Figure 3A:
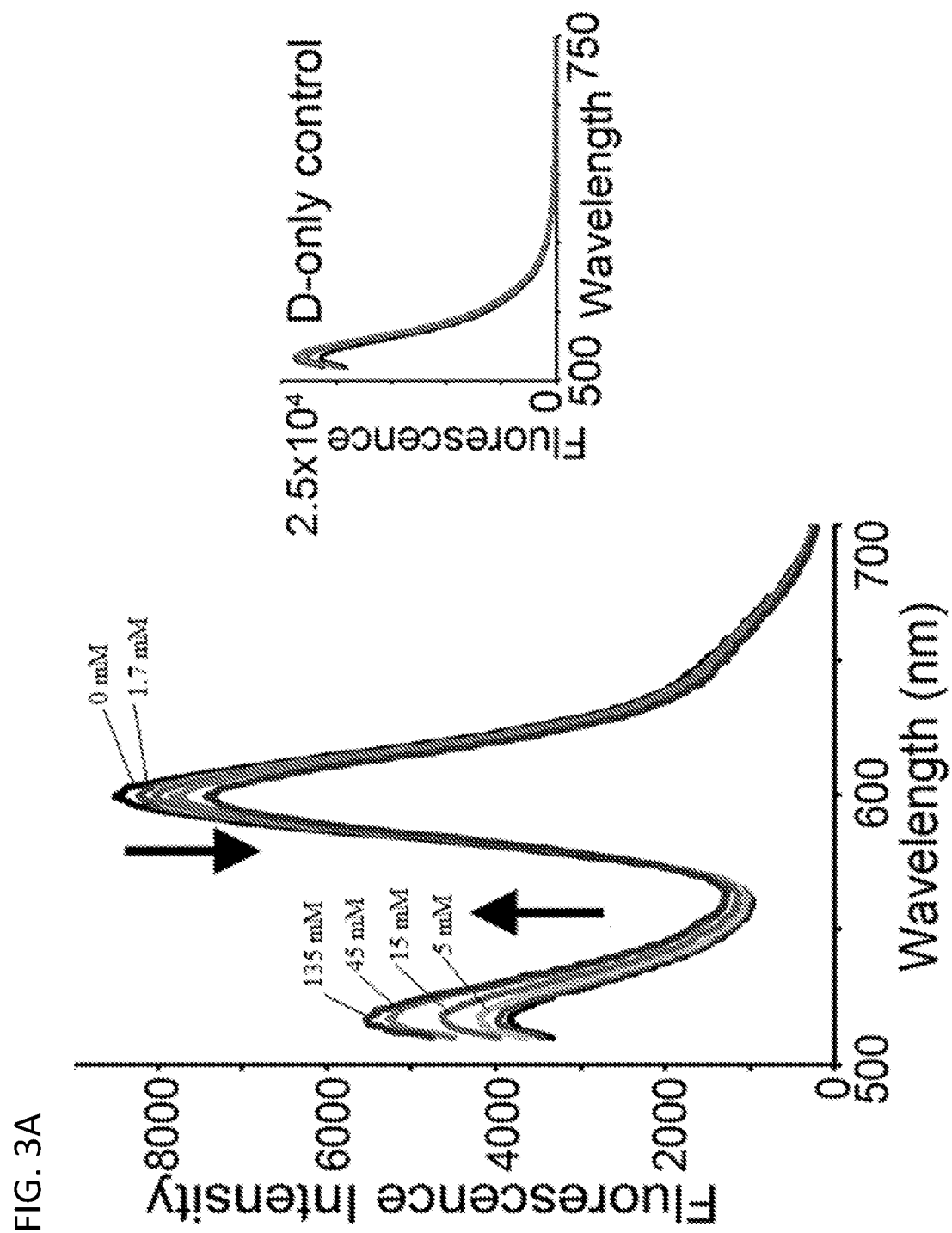
FIG. 3A. Steady-state ADP titration data performed at 25 nanomolar (nM) AurA with unphosphorylated FRET-labeled AurA C290S C393S ("AurA CL2") L225C S284C. Donor only-labeled AurA ("AurA+D") controls are shown in inset.

As further described in the Examples, for preparation of FRET-labeled AurA constructs, two positions in AurA were chosen for labeling with fluorophores: one mobile position in the activation loop (T287), and one immobile position on helix D (L225) (see FIG. 1). Using site-directed mutagenesis in an AurA construct with no other solvent-exposed Cys residues ("Cys-lite"), these two labeling positions were mutated to Cys. (All expression and mutagenesis protocols can be performed in *E. coli*; a 1 L culture routinely yields approximately 50 mg purified AurA.) These constructs were labeled with maleimide-functionalized donor fluorophore, and cation exchange chromatography was used to separate the desired singly-labeled AurA product from excess dye and unlabeled and doubly labeled protein. Finally, the remaining unreacted Cys was labeled with maleimide-functionalized A fluorophore. This approach reliably yielded homogeneously labeled samples, as measured by mass spectrometry (FIG. 2A). These samples were then tested for function using a commercially available fluorescence-based kinase assay (DiscoverX, Fremont, Calif.) (FIG. 2B), and tested for changes in FRET due to the AurA-specific activator peptide TPX2, which is known to stabilize an active conformation (see FIG. 2C and FIG. 3A for representative FRET data). Negligible aggregation of the labeled protein was observed using gel filtration chromatography, and FRET experiments with guanidinium HCl yielded similar unfolding curves to those obtained with wildtype AurA studied by Trp fluorescence.

The phosphorylation state of AurA can be controlled by making targeted mutations that influence the degree of autophosphorylation occurring during expression in *E. coli*. Specifically, a C290A mutation promotes phosphorylation, allowing isolation of homogeneously T288-phosphorylated AurA, whereas a C290S mutation inhibits phosphorylation, allowing isolation of homogeneously unphosphosphorylated enzyme (Burgess and Bayliss, *Acta. Cryst. F. Struct. Biol. Commun.*, 2015, 71(Pt 3):315-9). More generally, mutations can be made that influence the conformational state and activity level of a kinase, such as a mutation of a gatekeeper residue that arises in patients undergoing kinase inhibitor therapies. The effects of these mutations may be studied by the methods described herein.

Methods of Using the Protein Kinases

In another aspect, this disclosure provides methods for using a protein kinase described herein. For example, a protein kinase including a donor molecule and an acceptor molecule can be used to identify conformational changes involved in kinase regulation, that is, as an allostery sensor; to identify kinase-binding molecules including, for example, a kinase inhibitor; to identify cancer therapeutics; and/or for high-throughput screening.

At the time of the invention, models of the conformational changes involved in kinase activation were based largely on data collected by X-ray crystallography, a method which is intrinsically limited in its ability to show protein flexibility and dynamics. Activation loop structure in some conformational states (e.g., unphosphorylated AurA not bound to any ligands) has remained entirely inaccessible to this method due to high flexibility, leading to crystallographic disorder. Hydrogen/deuterium exchange mass spectrometry has provided some information about activation loop dynamics, but provides limited information about structure. Nuclear magnetic resonance (NMR) spectroscopy is a powerful method for exploring structural dynamics in solution, but it is expensive and its inherently slow timescale of measurement makes the activation loop a challenge to study. In contrast, the methods described herein enable rapid and clear observation of an entire population of activation loop conformations in solution under any condition at nanomolar concentrations, dramatically improving upon available methods for the study of allosteric regulation.

At the time of the invention, most currently available high-throughput screening assays measured substrate phosphorylation activity, and therefore must typically be performed with the kinase phosphorylated on the activation loop, locking the loop in an active conformation and preventing allosteric switching to inactive conformations. Hence, these assays are not suitable for detection of allosteric inhibition. In contrast, the methods described herein do not require activation loop phosphorylation of the kinase and specifically measure allosteric movements of the loop, making them superior for detecting allosteric inhibitors.

In one aspect, this disclosure describes a method that includes measuring the proportion of protein kinase in two or more conformations. For example, for a protein kinase that can exist in at least a first conformation and a second conformation, when the kinase is in the first conformation, energy is transferred from the donor molecule to the acceptor molecule; and when the kinase is in the second conformation, the efficiency with which energy is transferred from the donor molecule to the acceptor molecule differs from the efficiency with which energy is transferred from the donor molecule to the acceptor molecule in the first conformation. This disclosure describes a method that includes measuring the proportion of protein kinase in the first conformation and, in some embodiments, measuring the proportion of protein kinase in the second conformation. In some embodiments, the protein kinase can exist in additional conformations wherein in each conformation the efficiency with which energy is transferred from the donor molecule to the acceptor molecule differs from the efficiency with which energy is transferred from the donor molecule to the acceptor molecule in the other conformations, and the method can include measuring the proportion of protein kinase in each conformation. In some embodiments, the method can include measuring the distance between the two fluorophores and thus the position of the kinase activation loop, an important structural parameter of protein kinase drug targets. Measurement of the position of the kinase activation loop can allow discrimination of the effects of different subtypes of allosteric inhibitors and can provide direct information on the nature of the induced structural change. Because of this discriminatory ability, the described methods have potential to accelerate allosteric kinase inhibitor discovery.

In some embodiments, at least 0.1 percent, at least 0.5 percent, at least 1 percent, at least 2 percent, at least 3 percent, at least 5 percent, at least 10 percent, at least 20 percent, at least 30 percent, at least 40 percent, at least 50 percent, at least 60 percent, at least 70 percent, at least 80 percent, at least 90 percent, at least 95 percent, at least 98 percent, or at least 99 percent of the protein kinase adopts a first conformation. In some embodiments, up to 1 percent, up to 2 percent, up to 5 percent, up to 10 percent, up to 20 percent, up to 30 percent, up to 40 percent, up to 50 percent, up to 60 percent, up to 70 percent, up to 80 percent, up to 90 percent, up to 95 percent, up to 98 percent, up to 99 percent, or up to 100 percent of the protein kinase adopts a first conformation.

In some embodiments, at least 0.1 percent, at least 0.5 percent, at least 1 percent, at least 2 percent, at least 3 percent, at least 5 percent, at least 10 percent, at least 20 percent, at least 30 percent, at least 40 percent, at least 50 percent, at least 60 percent, at least 70 percent, at least 80 percent, at least 90 percent, at least 95 percent, at least 98 percent, or at least 99 percent of the protein kinase adopts a second conformation. In some embodiments, up to 1 percent, up to 2 percent, up to 5 percent, up to 10 percent, up to 20 percent, up to 30 percent, up to 40 percent, up to 50 percent, up to 60 percent, up to 70 percent, up to 80 percent, up to 90 percent, up to 95 percent, up to 98 percent, up to 99 percent, or up to 100 percent of the protein kinase adopts a second conformation.

In some embodiments, measuring the proportion of protein kinase in each conformation preferably comprises measuring Förster resonance energy transfer (FRET) from the donor molecule to the acceptor molecule. In some embodiments, the distance between the donor molecule and the acceptor molecule in different conformations differs by at least 1 Angstrom (Å), at least 2 Å, at least 3 Å, at least 4 Å, or at least 5 Å. For example, in the second conformation, the distance between the donor molecule and the acceptor molecule differs by at least 1 Å, at least 2 Å, at least 3 Å, at least 4 Å, or at least 5 Å from the distance between the donor molecule and the acceptor molecule when the protein kinase is in the first conformation.

Measuring FRET can include acquiring a steady-state (SS) FRET measurement, which measures time-averaged total fluorescence emission detected over any range of emission wavelengths, utilizing any suitable instrumentation for acquiring time-averaged total fluorescence emission detected over any range of emission wavelengths. Measuring FRET can additionally or alternatively include acquiring a time-resolved (TR) FRET measurement, which detects the donor fluorophore time-dependent emission waveform after a single excitation pulse. TR-FRET can be measured using direct waveform recording as described in Muretta et al. (Rev Sci Instrum, 2010, 81(10):103101), but also by time-correlated single photon counting as described in Muretta et al. (Rev Sci Instrum, 2010, 81(10):103101), or by frequency domain modulation as described in Lokowicz J R, Principles of Fluorescence Spectroscopy, Springer (third edition).

Using a FRET assay that is highly sensitive to changes in the conformation of the kinase including, for example the activation loop, allows for the determination of the conformational preferences of kinase inhibitors in solution. The high-throughput nanosecond time-resolved FRET acquired by direct waveform recording or high-throughput steady-state emission spectra acquired by spectral recording plate readers can provide particularly relevant information as they enable the rapid measurement of small molecule inhibitor binding with high signal-to-noise and well to well coefficient of variance of lower than 1 percent at nanomolar protein concentrations. In some embodiments, laser excitation can be used for high-sensitivity spectral recording. In some embodiments, direct waveform recording (Muretta et al. Rev Sci Instrum, 2010, 81(10):103101) can be used to capture and compare fluorescence lifetime waveforms generated by a pulsed laser directed onto a sample including the protein kinase. Use of direct waveform recording yields excellent signal-to-noise at recording rates of 25 wells/second and at sample concentrations as low as 1 nM.

Figure 3B:
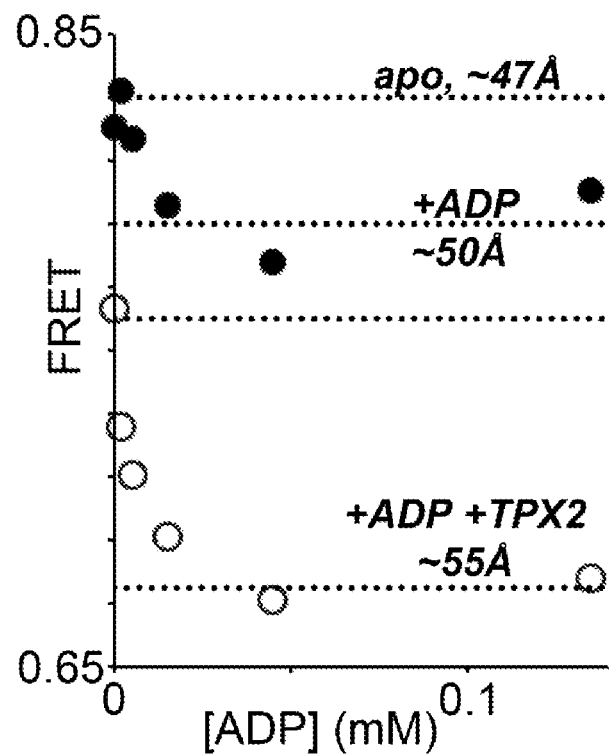
FIG. 3B. Calculation of FRET based on steady-state data as shown in FIG. 3A. Distances assigned based on the equation FRET=$R_0^6/(1+(r/R_0)^6)$, where $R_0$ for the Alexa 488/Alexa 568 pair used is 62 Å.
Figure 3D:
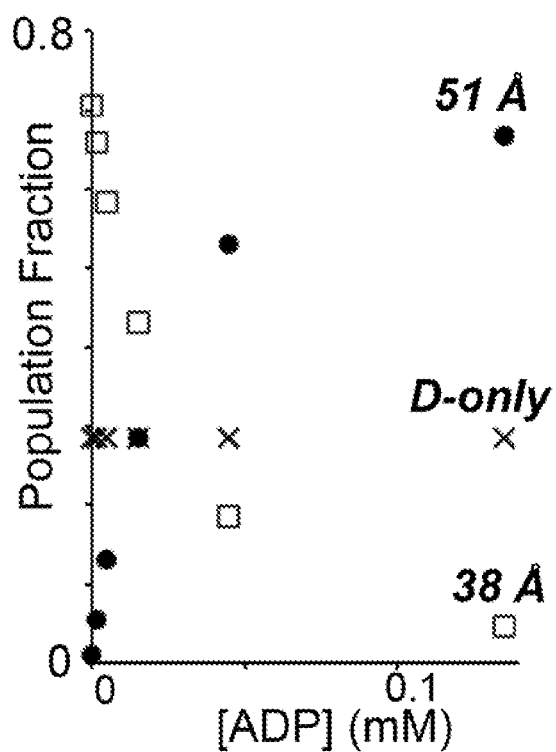
FIG. 3D. Population fitting data for a representative time-resolved FRET ADP titration experiment. Data were fit by a two state structure-based model using iterative convolution and least squares optimization as described in Muretta et al. (*Proc Natl Acad Sci USA*, 2015, 112(47):14593-8). In this model, the measured time-resolved FRET of donor+acceptor labeled AurA is described by a function composed of the sum of three components: Donor only (D-only, constant; x), and FRET-labeled with FRET distances 38 Å (white squares) and 51 Å (black circles).

Using steady-state FRET (SS FRET) to investigate the conformations of AurA in the presence and absence of nucleotides and TPX2 in solution (FIG. 2, FIG. 3A, FIG. 3B), the addition of ADP to apo AurA (that is, AurA not bound to any ligands) was found to reduce FRET, indicating that nucleotide binding alone shifts the activation loop to a more active conformation. Based on the published $R_0$ for this FRET pair (D: Alexa 488; A: Alexa 568 (ThermoFisher, Waltham, Mass.)), the population average R was calculated to increase approximately 3 Å. TPX2 also reduces FRET, and, when added together, these ligands induce a total decrease in FRET corresponding to an approximately 8 Å increase in R. These distance changes are consistent with published crystal structures.

Figure 4A:
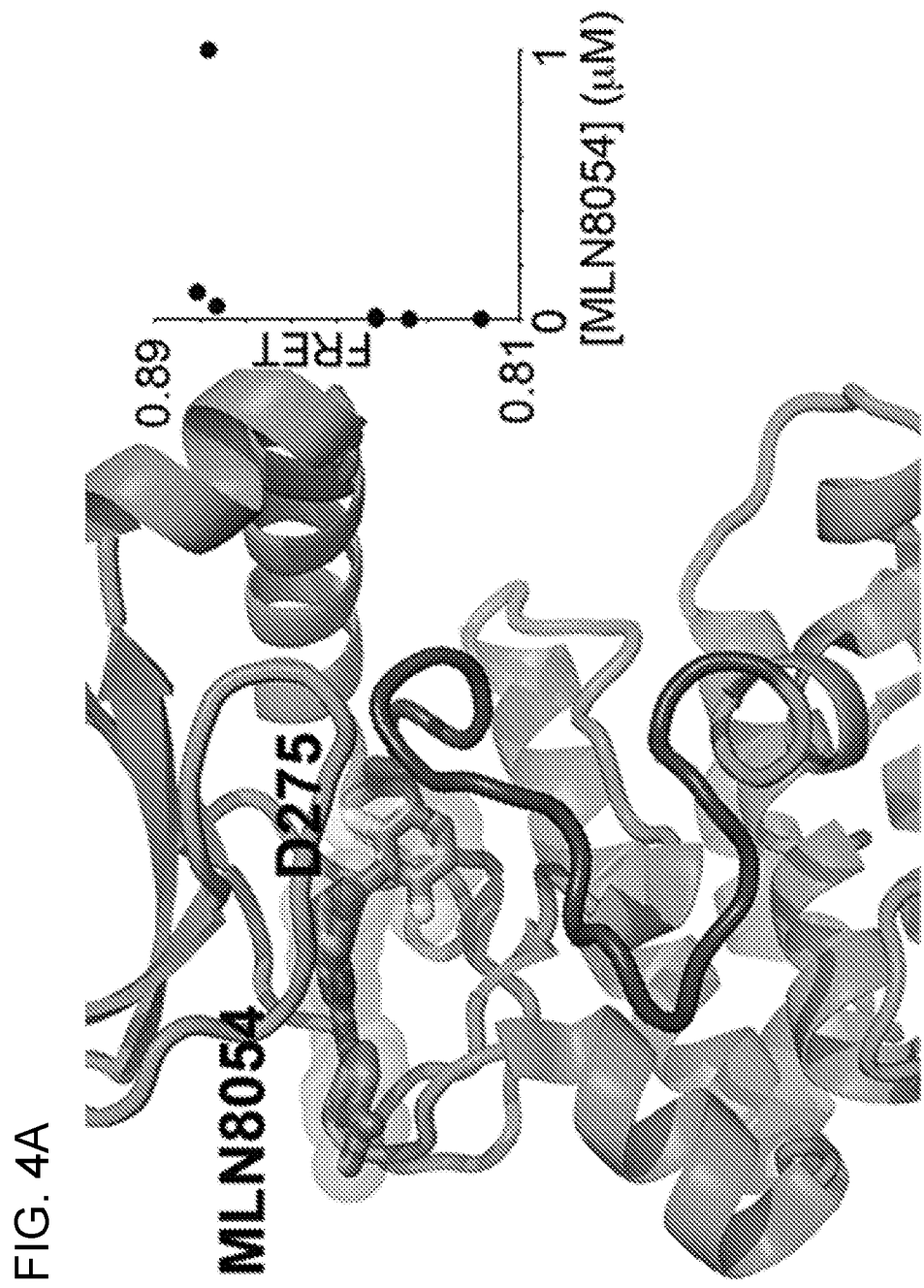
FIG. 4A. MLN8054 (Selleck Chemicals, Houston, Tex.), a potent and selective inhibitor of Aurora A, binds DFG-out AurA (PDB ID 2WTV).
Figure 4B:
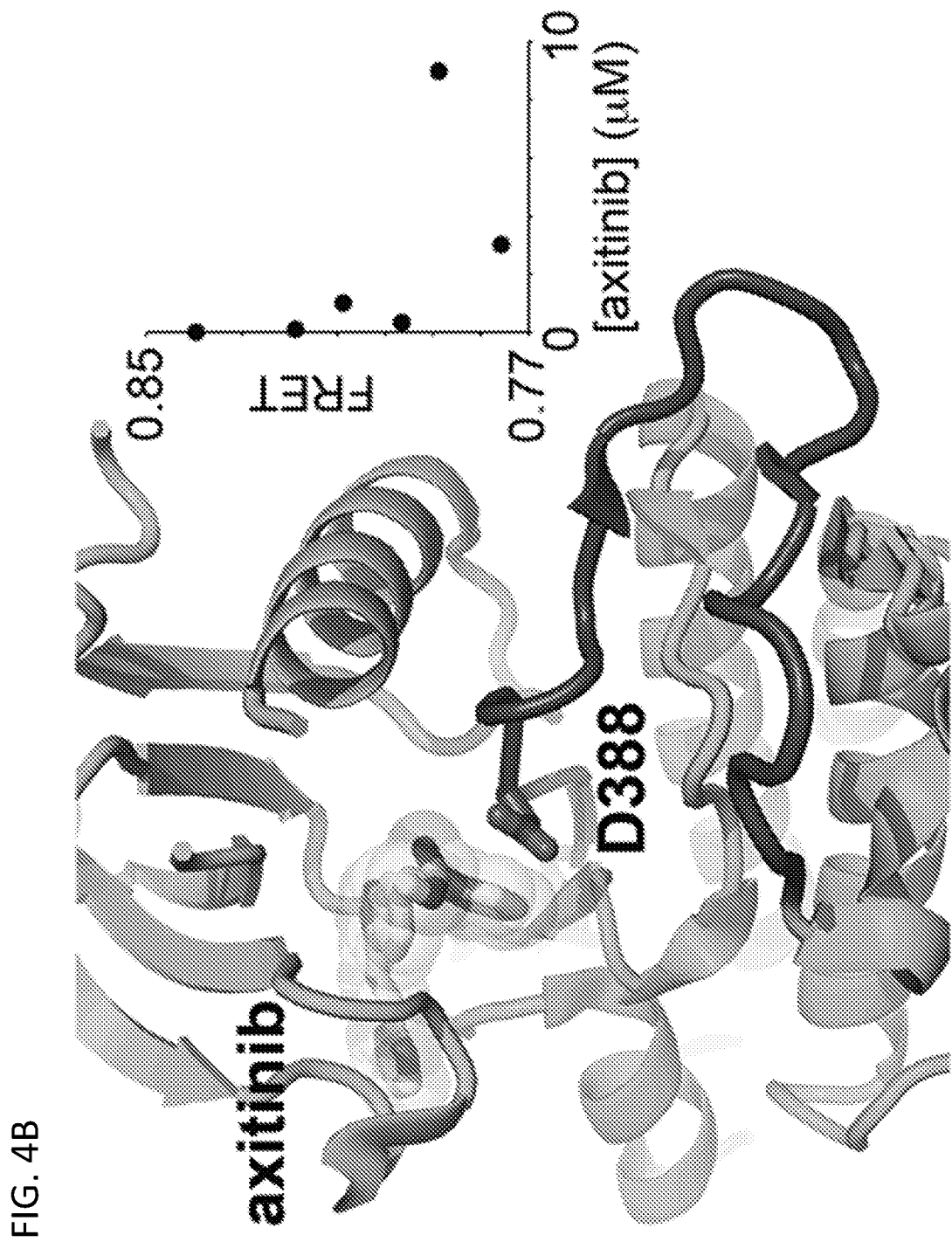
FIG. 4B. Axitinib binds DFG-In BCR Ab1 T315I. PDB ID 4TWP. (Note that no crystal structure for axitinib bound to AurA has been obtained.) Insets: inhibitor binding to FRET-labeled AurA. Note: FRET assays were performed with two different labeling preps, giving slightly different FRET values.

The conformational effects of approximately 30 commercially available inhibitors of AurA were investigated using SS FRET. Many of these inhibitors (including VX680) induced no observable change in the conformation of AurA, but several did, including two examples shown in FIG. 4. The addition of the inhibitor MLN8054 to apo AurA (that is, AurA not bound to any ligands) resulted in an increase in FRET (FIG. 4A), in agreement with crystallography data that show the inhibitor's extensive contacts with the "Asp-Phe-Gly (DFG)" motif move the activation loop into a highly inhibited position. When the kinase assumes a catalytically inactive conformation, the DFG motif at the N terminus of the activation loop is flipped "out" relative to its conformation in the active state ("in"). By contrast, binding of the inhibitor axitinib reduces FRET, to a similar degree as ADP (FIG. 4B). No AurA-axitinib crystal structure has been reported, but these data suggest axitinib induces a DFG-In conformation, as observed with BCR-ABL1 T315I-axitinib.

Figure 3C:
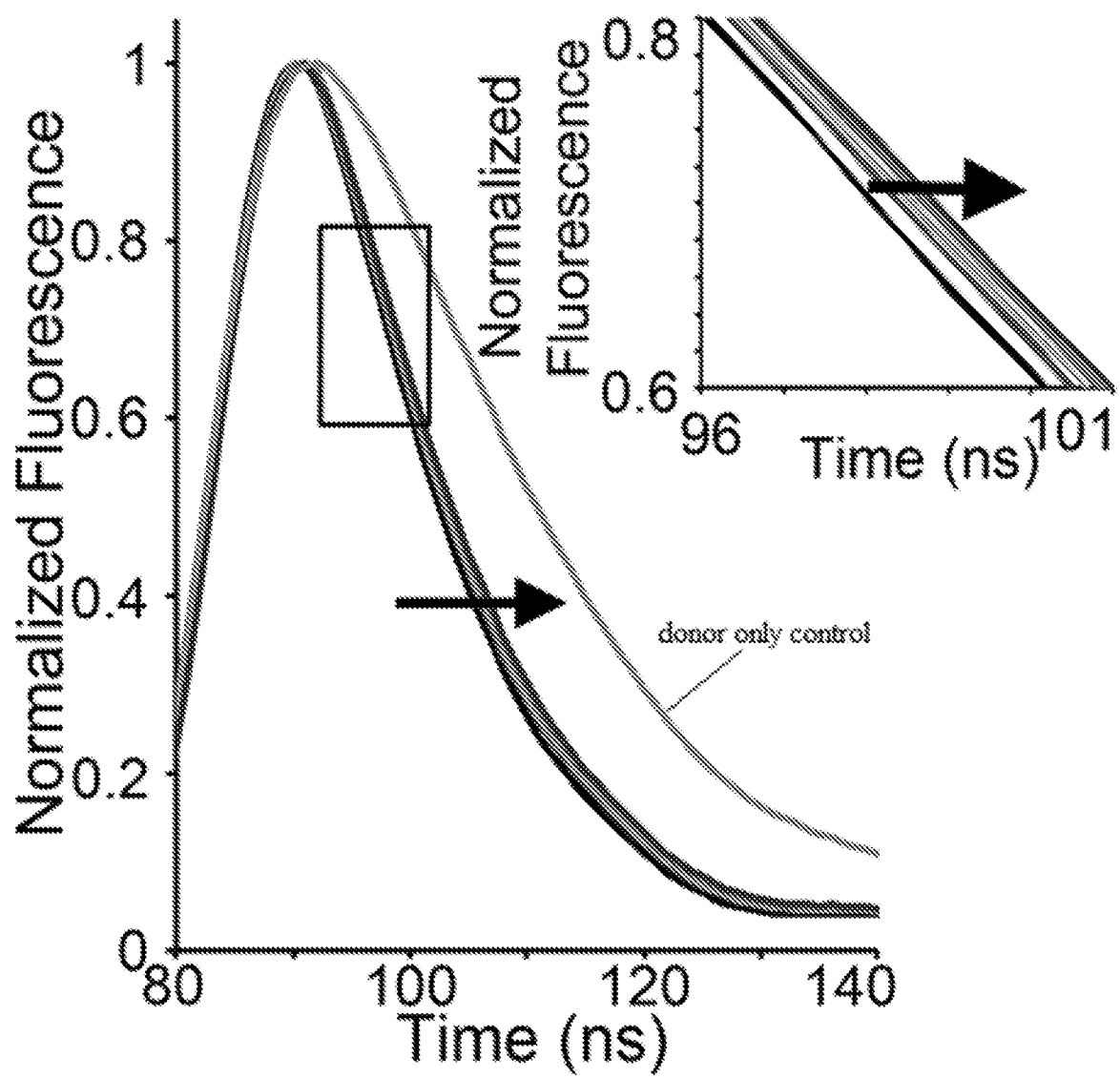
FIG. 3C. Time-resolved (TR) FRET ADP titration data performed at 50 nM AurA CL2 L225C T287C unphosphorylated, in the presence of 10 $\mu$M TPX2. Inset shows expansion of box shown in larger plot. Arrows indicate increasing ADP concentration. Experiment was performed in a 384 well plate; measurement was performed using a high-throughput nanosecond time-resolved fluorescence spectrophotometer using direct waveform recording. Details of this instrument can be found in Cornea et al. (*J Biomol Screen*, 2013, 18(1):97-107) and Petersen et al. (*Rev Sci Instrum*, 2014, 85(11):113101). Details of the methodology of direct waveform recording based time-resolved fluorescence measurements can be found in Muretta et al. (*Rev Sci Instrum*, 2010, 81(10):103101). Experimental buffer was ADP Quest assay buffer containing no bovine gamma ($\gamma$) globulins with 1 percent (%) DMSO added.

In time-resolved FRET (TR-FRET), each individual state of the donor fluorophore with distinct photophysical decay properties (including rates of energy transfer to an acceptor fluorophore) contributes to the emission waveform with its own exponential lifetime and an amplitude corresponding to the contributing mole fraction. The mole fractions and lifetime of each subpopulation can then be determined using population modeling and data fitting. Measurements using TR-FRET show an increase in average fluorescence lifetime (a decrease in FRET) upon addition of TPX2 or ADP to labeled AurA (FIG. 3C). These data can be analyzed and fit to structural models to calculate the distribution of FRET distances present in each sample (see, for example, FIG. 3C, FIG. 3D, and FIGS. 8-10).

In some embodiments, a method of using the protein kinase can include exposing the protein kinase to a small molecule. In some embodiments, a method of using the protein kinase can include exposing the protein kinase to a panel of small molecules. In some embodiments, when the protein kinase is contacted with the small molecule under conditions such that a covalent bond is formed between the kinase and the small molecule. The small molecule can include, for example, at least one of a nucleotide, an activator protein, an activator peptide, or a small-molecule allosteric modulator. The method can further include determining the proportion of a conformation adopted by the protein kinase when the small molecule is in contact with the protein kinase. Determining the effect or effects of one or more small molecules on the conformation or proportions of conformations adopted by a protein kinase can be used to identify small molecules that bind to the kinase. In some embodiments, determining the effect of a small molecule on the conformation adopted by a protein kinase can be used to determine if that small molecule inhibits the kinase or activates the kinase. In some embodiments, determining the effects of each member of a library of small molecules can be used to determine which members of the library have inhibitory effects on the kinase and/or act as an allosteric kinase inhibitor. For example, determining the effect of a small molecule on the conformation adopted by a protein kinase can be used to screen for an allosteric small molecule or a peptide-based drug that cause specific inhibitory structural changes in the target protein kinase. In some embodiments, the method can include high-throughput screening. A FRET assay as described herein is highly sensitive to changes in the conformation of a kinase (e.g., AurA) and does not require activation loop phosphorylation, providing an improvement over currently available high-throughput screening technologies for the detection of allosteric inhibitors.

Figure 11A:
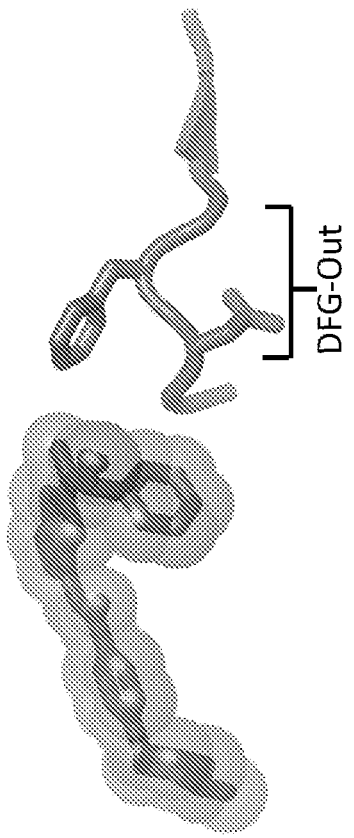
FIG. 11(A-C) shows X-ray structures of AurA bound to three of the inhibitors investigated by FRET, confirming the FRET-based DFG-In/Out assignments for these compounds shown in FIG. 10. The two DFG-Out compounds danusertib and MLN-8054 yielded short FRET distances, consistent with DFG-Out; whereas the DFG-In compound SNS314 yielded a long FRET distance, consistent with DFG-In (see FIG. 10). The crystal structures of FIG. 11A and FIG. 11B show Danusertib and MLN8054 bound to AurA, respectively, and show that these compounds bind to the DFG-out conformation of AurA.
FIG. 11C shows the crystal structure of AurA in the presence of SNS-314, and shows AurA displays a DFG-in conformation.
Figure 11B:
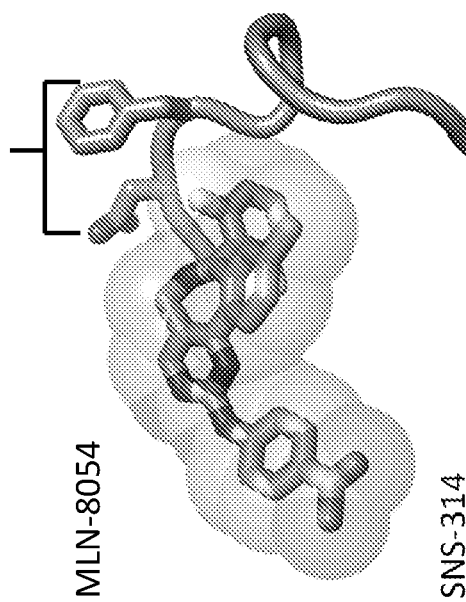
Figure 11C:
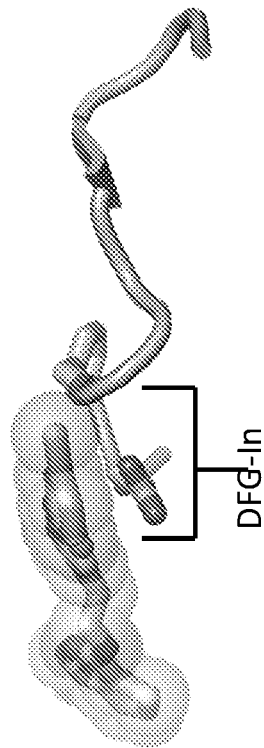

For example, as shown in FIG. 10, FIG. 11, and FIG. 12, the effects of inhibitors on kinase conformation, and the conformational preferences of kinase inhibitors can be detected using TR-FRET and the methods described herein. The methods described herein also have the capability to distinguish between compounds (e.g., inhibitors) that promote a homogeneous structural state and compounds that induce a conformational equilibrium.

Figure 5A:
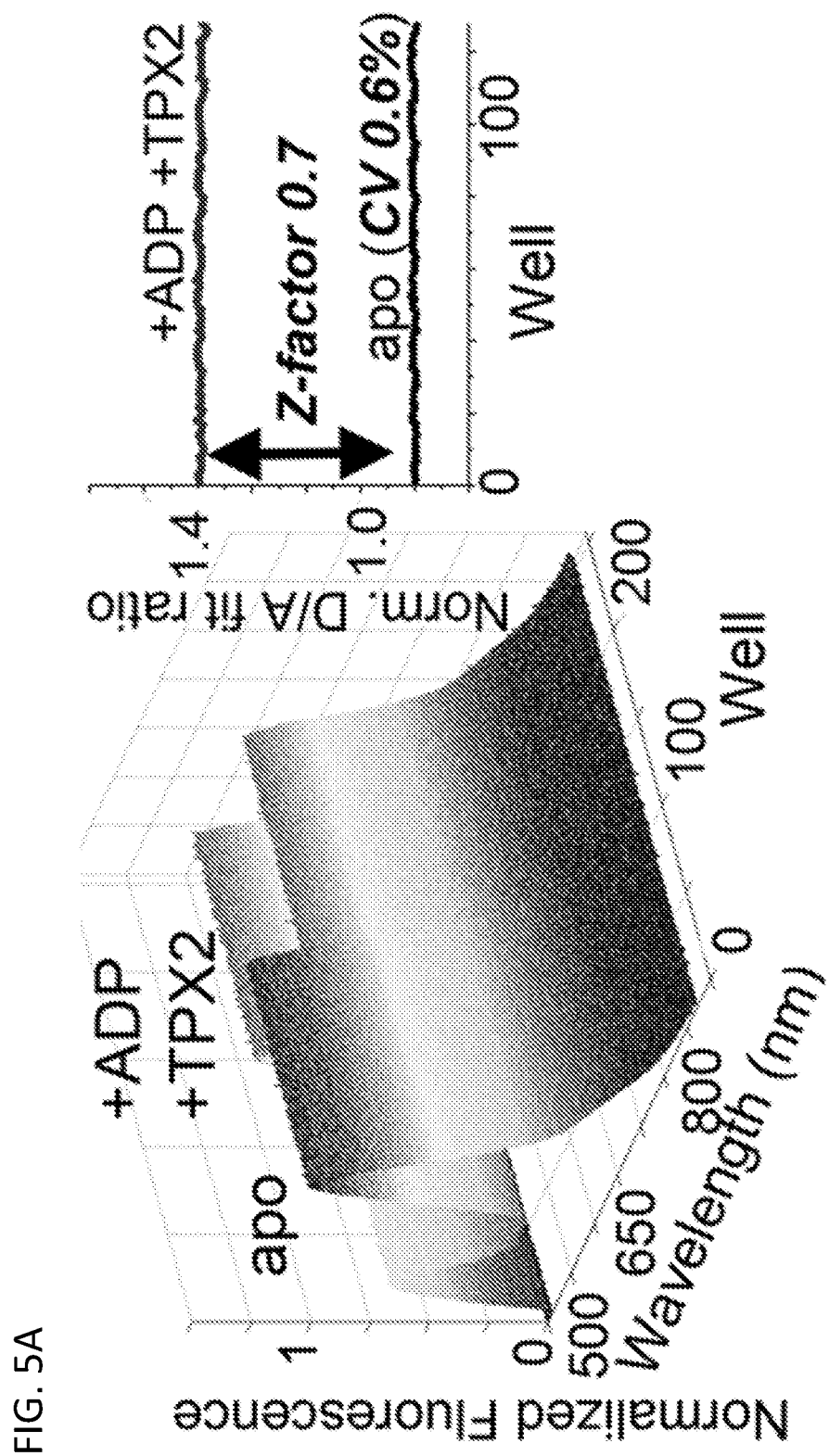
FIG. 5A. Control experiment comparing spectral plate reader signal for 128 wells each of free inactive FRET-labeled AurA CL2 L225C T287C vs. activated AurA (+100 $\mu$M ADP+10 $\mu$M TPX2). Inset shows coefficient of variance <1% and the calculated Z-factor for the experiment; a Z-factor >0.5 is considered the standard for high-throughput screening, indicating the feasibility a FRET assay for this purpose.
Figure 5B:
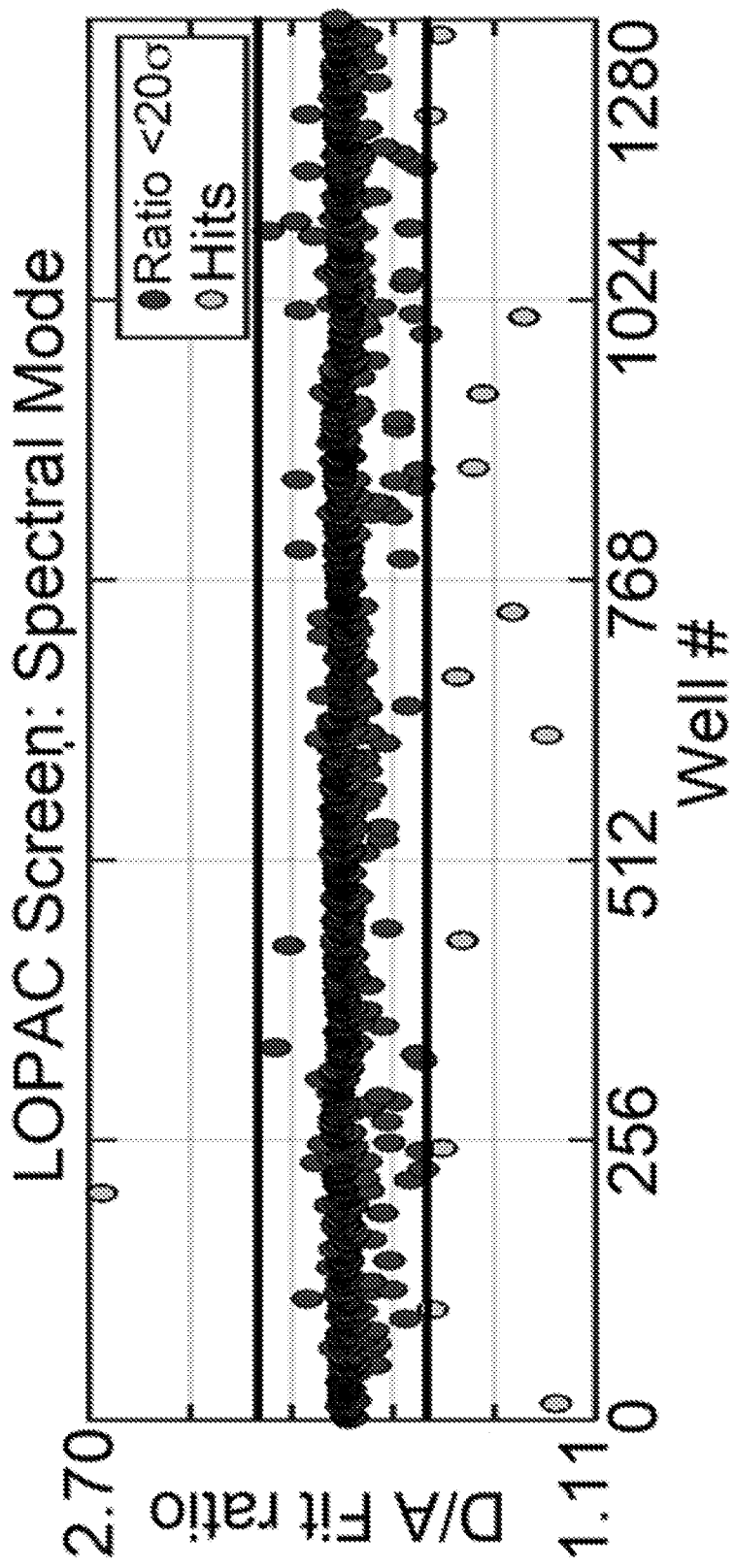
FIG. 5B. Library of Pharmacologically Active Compounds (LOPAC) screen, read on a high-throughput nanosecond time-resolved FRET direct waveform recording plate reader or a steady-state fluorescence emission spectral recording plate reader. Hits outside 20$\sigma$ (solid lines) are shown in light gray.

As shown in FIG. 5, use of a high-throughput FRET assay yielded a coefficient of variation (CV) of less than 1.0 percent (%) and a Z-factor of greater than 0.5 (CV and Z-factor are metrics of assay robustness) for both lifetime and spectral emission modes spectral data, as shown in FIG. 5A. When screening against the industry standard LOPAC validation library (1280 compounds, Sigma Aldrich, St. Louis, Mo.) in both time-resolved and spectral modes (spectral read shown FIG. 5A) the assay robustly detected known kinase inhibitors.

Figure 6A:
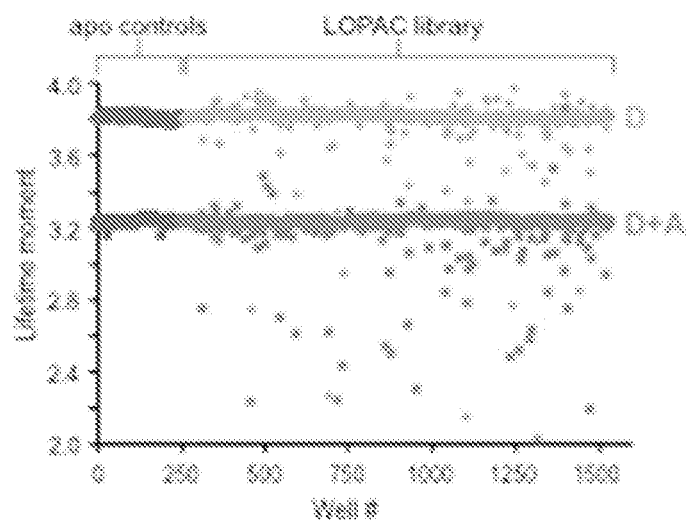
FIG. 6A. Lifetime moments calculated for controls and LOPAC screen library samples.
Figure 6B:
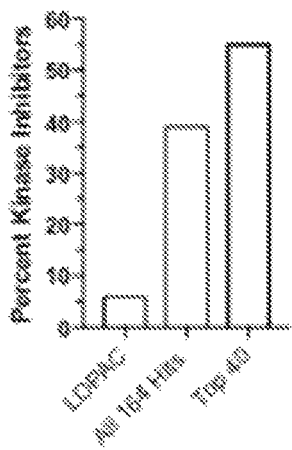
FIG. 6B. Screen hits were defined as ±5$\sigma$ from the AurA+D and/or donor- and acceptor-labeled (AurA+D+A) control lifetimes. These hits were highly enriched for known kinase inhibitors relative to the entire LOPAC library, validating the feasibility of the assay for finding new kinase inhibitor candidates.
Figure 6C:
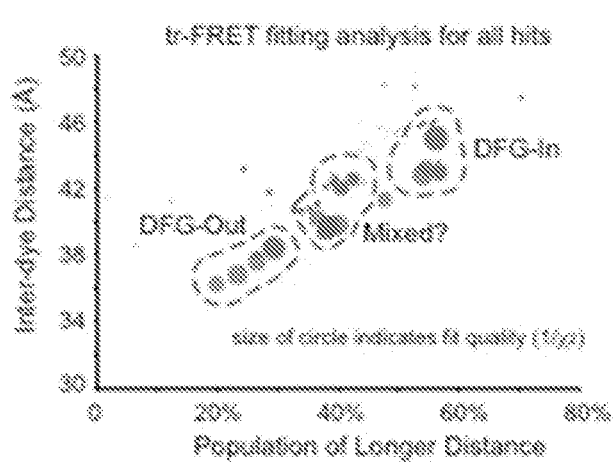
FIG. 6C. Comparison of fits to single FRET distance and two FRET distance models of LOPAC library hits. Data were fit to either two-state or one-state structure-based models using iterative convolution and least squares optimization as described in Muretta et al. (*Proc Natl Acad Sci USA*, 2015, 112(47):14593-8) using a single distance model (y-axis) and a two-distance model with distances 33 Angstroms (Å) and 55 Å (populations denoted by x-axis). The radius of each circle scales with the goodness of fit to the single-distance model as determined by the fit $\chi^2$; thus, hits which do not fit well to this model are observed as small points.

As shown in FIG. 6, the apo and activated controls and LOPAC library screen lifetime data were analyzed according to lifetime moment (FIG. 6A). The CV for the lifetime controls was determined to be less than 0.5%, and screen hits were defined as ±5σ from the donor- and/or FRET-labeled AurA control lifetimes. These screen hits were highly enriched for known kinase inhibitors relative to the entire LOPAC library (FIG. 6B). The time-resolved fluorescence emission waveforms for screening hits were fitted using published methods (Muretta et al. *Proc Natl Acad Sci USA*, 2015, 112(47):14593-8) to two different models: one incorporating a single FRET distance (FIG. 6C, y-axis), and one incorporating two FRET distances of 33 Angstroms (Å) and 55 Å, each with its own population fraction (populations denoted by x-axis). In FIG. 6C, the radius of each circle scales with the goodness of fit to the single-distance model as determined by $\chi^2$; thus, hits which do not fit well to this model are observed as small circles or points. Replicate screens of the LOPAC library (FIG. 13) performed in 1536-well plates show that the results are exceptionally robust and reproducible even when applied in a high-throughput format, confirming the feasibility of large-scale screening efforts using the methods described herein.

In some embodiments, including, for example, when the kinase includes a mutation, the kinase can be used to identify an allosteric inhibitor specific for a kinase that has developed resistance to an existing drug or treatment. Additionally or alternatively, a kinase including a mutation can be used to determine the effect of the mutation on allosteric regulation, including, but not limited to, mutation of the gatekeeper residue in the active site of the kinase.

Exemplary Protein Kinase Embodiments

Embodiment 1. A protein kinase comprising a donor molecule and an acceptor molecule,
wherein the protein kinase can exist in at least a first conformation and a second conformation; and
wherein when the kinase exists in the first conformation, energy is transferred from the donor molecule to the acceptor molecule with higher efficiency than when the kinase exists in the second conformation.

Embodiment 2. The protein kinase of Embodiment 1, wherein when the donor molecule comprises a fluorophore.

Embodiment 3. The protein kinase of either Embodiment 1 or Embodiment 2, wherein the acceptor molecule comprises a fluorophore.

Embodiment 4. The protein kinase of any one of Embodiments 1 to 3, wherein the donor molecule comprises AlexaFluor 488.

Embodiment 5. The protein kinase of any one of Embodiments 1 to 4, wherein the acceptor molecule comprises AlexaFluor 568.

Embodiment 6. The protein kinase of any one of Embodiments 1 to 5, wherein, in the first conformation, energy is transferred from the donor molecule to the acceptor molecule via Förster resonance energy transfer (FRET).

Embodiment 7. The protein kinase of any one of Embodiments 1 to 6, wherein at least one of the donor molecule and the acceptor molecule are covalently linked to the protein kinase.

Embodiment 8. The protein kinase of any one of Embodiments 1 to 7, wherein at least one of the donor molecule and the acceptor molecule binds an ATP-binding site of the protein kinase.

Embodiment 9. The protein kinase of any one of Embodiments 1 to 8, wherein at least one of the donor molecule and the acceptor molecule are covalently linked to the activation loop, the alpha-C helix, the D helix, or the phosphate binding P-loop of the protein kinase.

Embodiment 10. The protein kinase of any one of Embodiments 1 to 9, wherein the protein kinase comprises an Aurora kinase.

Embodiment 11. The protein kinase of any one of Embodiments 1 to 10, wherein the protein kinase comprises Aurora A (AurA).

Embodiment 12. The protein kinase of any one of Embodiments 1 to 11, wherein the protein kinase is phosphorylated.

Embodiment 13. The protein kinase of any one of Embodiments 1 to 12, wherein the protein kinase is bound to at least one of a nucleotide, an activator protein, an activator peptide, or a small-molecule allosteric modulator.

Embodiment 14. The protein kinase of any one of Embodiments 1 to 13, wherein when the kinase is in the second conformation, the distance between the donor molecule and the acceptor molecule differs by at least 1 Angstrom (Å) from the distance between the donor molecule and the acceptor molecule when the protein kinase is in the first conformation.

Embodiment 15. The protein kinase of any one of Embodiments 1 to 14, wherein the kinase can exist in additional conformations, wherein the distance between the donor molecule and the acceptor molecule of each conformation differs by at least 1 Angstrom (Å) from the distance between the donor molecule and the acceptor molecule of the other conformations.

Embodiment 16. A method of making the protein kinase of any one of Embodiments 1 to 15.

Exemplary Embodiments of Methods of Making the Protein Kinase

Embodiment 1. A method comprising covalently linking a protein kinase to a donor molecule and an acceptor molecule.

Embodiment 2. The method of Embodiment 1, wherein at least one of the donor molecule and the acceptor molecule are covalently linked to a residue of the activation loop, the P-loop, the D-helix, or the C-helix of the protein kinase.

Embodiment 3. The method of either Embodiment 1 or Embodiment 2, wherein covalently linking the protein kinase to at least one of the donor molecule and the acceptor molecule comprises reacting a thiol with a maleimide, an azide with an alkyne, or an aldehyde with a hydrazine or a hydroxylamine.

Embodiment 4. The method of any of Embodiments 1 to 3, wherein covalently linking the protein kinase to at least one of the donor molecule and the acceptor molecule comprises native chemical ligation and/or intein-mediated protein splicing.

Embodiment 5. The method of either Embodiment 1 or Embodiment 2, wherein covalently linking the protein kinase to the donor molecule or the acceptor molecule comprises co-translational incorporation of an amino acid.

Embodiment 6. The method of Embodiment 4, wherein the method comprises incorporating the amino acid by nonsense suppression.

Embodiment 7. The method of either of Embodiments 5 or 6, wherein the method comprises incorporating a fluorescent amino acid.

Exemplary Embodiments of Methods of Using the Protein Kinase

Embodiment 1. A method comprising:
providing a protein kinase comprising a donor molecule and an acceptor molecule, wherein the protein kinase can exist in at least a first conformation and a second conformation;
wherein in the first conformation, energy is transferred from the donor molecule to the acceptor molecule;
wherein in the second conformation, the efficiency with which energy is transferred from the donor molecule to the acceptor molecule differs from the efficiency with which energy is transferred from the donor molecule to the acceptor molecule in the first conformation; and
measuring the proportion of protein kinase in the first conformation.

Embodiment 2. The method of Embodiment 1, wherein measuring the proportion of protein kinase in the first conformation comprises measuring Förster resonance energy transfer (FRET) from the donor molecule to the acceptor molecule.

Embodiment 3. The method of Embodiment 2, wherein measuring FRET comprises acquiring a steady-state FRET measurement.

Embodiment 4. The method of either of Embodiment 1 or Embodiment 2, wherein measuring FRET comprises acquiring a time-resolved FRET measurement.

Embodiment 5. The method of any one of Embodiments 1 to 4, wherein the method further comprises measuring the proportion of protein kinase in the second conformation.

Embodiment 6. The method of any one of Embodiments 1 to 5, wherein when the kinase is in the second conformation, the distance between the donor molecule and the acceptor molecule differs by at least 1 Angstrom (Å) from the distance between the donor molecule and the acceptor molecule when the protein kinase is in the first conformation.

Embodiment 7. The method of any one of Embodiments 1 to 6,
wherein the protein kinase can exist in a third conformation,
wherein when the kinase is in the third conformation, the efficiency with which energy is transferred from the donor molecule to the acceptor molecule differs from the efficiency with which energy is transferred from the donor molecule to the acceptor molecule in the first conformation and differs from the efficiency with which energy is transferred from the donor molecule to the acceptor molecule in the second conformation, and
wherein the method further comprises measuring the proportion of protein kinase in the third conformation.

Embodiment 8. The method of Embodiment 7, wherein when the kinase is in the third conformation, the distance between the donor molecule and the acceptor molecule differs by at least 1 Angstrom (Å) from the distance between the donor molecule and the acceptor molecule when the protein kinase is in the first conformation and differs by at least 1 Å from the distance between the donor molecule and the acceptor molecule when the protein kinase is in the second conformation.

Embodiment 9. The method of any one of Embodiments 1 to 8, wherein the method comprises exposing the protein kinase to at least one of a nucleotide, an activator protein, an activator peptide, or a small-molecule allosteric modulator.

Embodiment 10. The method of any one of Embodiments 1 to 9, further comprising
providing a small molecule,
contacting the protein kinase with the small molecule,
determining the proportion of a first conformation adopted by the protein kinase when the small molecule is in contact with the protein kinase.

Embodiment 11. The method of Embodiment 10, wherein at least 0.1 percent, at least 0.5 percent, at least 1 percent, at least 2 percent, at least 3 percent, at least 5 percent, at least 10 percent, at least 20 percent, at least 30 percent, at least 40 percent, at least 50 percent, at least 60 percent, at least 70 percent, at least 80 percent, at least 90 percent, at least 95 percent, at least 98 percent, or at least 99 percent of the protein kinase adopts a first conformation.

Embodiment 12. The method of Embodiment 10 or Embodiment 11, wherein, up to 1 percent, up to 2 percent, up to 5 percent, up to 10 percent, up to 20 percent, up to 30 percent, up to 40 percent, up to 50 percent, up to 60 percent, up to 70 percent, up to 80 percent, up to 90 percent, up to 95 percent, up to 98 percent, up to 99 percent, or up to 100 percent of the protein kinase adopts a first conformation.

Embodiment 13. The method of any one of Embodiments 10 to 12, wherein the protein kinase is contacted with the small molecule under conditions such that a covalent bond is formed between the kinase and the small molecule.

Embodiment 14. The method of any one of Embodiments 10 to 13, wherein determining the proportion of a first conformation comprises measuring the position of an activation loop of the protein kinase.

The present invention is illustrated by the following examples. It is to be understood that the particular examples, materials, amounts, and procedures are to be interpreted broadly in accordance with the scope and spirit of the invention as set forth herein.

EXAMPLES

All reagents, starting materials and solvents used in the following examples were purchased from commercial suppliers (e.g., Sigma-Aldrich Chemical Company, St. Louis, Mo.) and were used without further purification unless otherwise indicated.

Example 1

Protein Purification:

All Aurora A (AurA) kinase domain constructs (human Aurora A, residues 122-403, containing an N-terminal hexahistidine tag; original WT construct provided by Elena Conti) were expressed in BL21-DE3-RIL cells (Agilent Technologies, Santa Clara, Calif.) at 18° C. overnight. Cells were pelleted and resuspended in lysis buffer (50 mM Tris pH 8.0, 500 mM NaCl, 10% glycerol, 20 mM imidazole) and lysed using an Emusiflex C3 (Avestin, Inc., Ottawa, ON, Canada). Lysate was then centrifuged at 20,000 rpm for 1 hour and loaded onto Ni NTA column (GE Healthcare Bio-Sciences, Pittsburgh, Pa.), washed with lysis buffer, and eluted with elution buffer (20 mM HEPES pH 7.5, 200 mM NaCl, 10% glycerol, 500 mM imidazole). Eluted AurA was then desalted into desalting buffer (300 mM NaCl, 10% glycerol, 20 mM HEPES pH 7.5).

Protein samples were then dephosphorylated for approximately 48 hours at 4° C. using Lambda Protein Phosphatase (LPP) (New England Biolabs, Ipswich, Mass.), and were then reduced using 10 mM dithiothreitol (DTT) for 15 minutes. The unphosphorylated AurA was purified by cation exchange chromatography after diluting approximately 20-fold into buffer A (100 mM NaCl, 10% glycerol, 20 mM HEPES, pH 7.5) using a HiTrap SP cation exchange column (GE Healthcare Bio-Sciences, Pittsburgh, Pa.) and eluted with a 20 column volume gradient from 0% to 100% buffer B (1 M NaCl, 10% glycerol, 20 mM HEPES pH 7.5). Aliquots of purified protein were flash frozen and stored at −80° C.

Kinase Activity Assays:

Kinase activities of purified proteins were measured using a coupled kinase assay (DiscoverX Corporation, Fremont, Calif.). Reactions were carried out in the ADP Quest Assay buffer (15 mM HEPES, pH 7.4, 20 mM NaCl, 1 mM EGTA, 0.02% TWEEN 20, 10 mM $MgCl_2$, and 0.1 mg/mL bovine-γ-globulins). Assays were performed using 10 μM TPX2 (residues 1-43, Selleck Chemicals, Houston, Tex.), and 1 mM kemptide peptide substrate (Anaspec Inc., Fremont, Calif.). Reactions were initiated by adding 50 μM ATP to each well of a 96-well black microplate (Corning Inc., Corning, N.Y.). Samples were incubated at 30° C. in a fluorescence plate reader (Tecan INFINITE M1000 PRO, Tecan Group Ltd., Mannedorf, Switzerland) for 30 minutes before starting reactions. Samples were excited at 500 nanometer (nm) and fluorescence emission recorded at 590 nm every 20 seconds for 240 cycles. Kinase activity was determined as the difference in activity between the samples with and without peptide substrate.

Cys-Lite Constructs and Mutagenesis for Labeling:

Cysteine residues observed to be solvent-exposed in published crystal structures were mutated to serines, forming a Cys-lite construct of AurA having two cystine sites mutated ("AurA CL2"), AurA C290S C393S, using the QuikChange Lightning Site-Directed Mutagenesis Kit (Agilent Technologies, Santa Clara, Calif.); use of this mutant for chemical modification of the protein has been previously described (Rowan et al., ACS Chem. Bio. 2013, 8(10):2184-91). Similar results were obtained with AurA C290S C393S C247S ("AurA CL3"), and this Cys-lite background is used for some experiments reported here (see, e.g., FIG. 3); however, for fluorophore labeling protocols, AurA CL2 was found to be sufficient.

Two labeling sites were chosen for FRET labeling: one immobile site, and one mobile site on the kinase activation loop. Mobility was estimated based on published crystal structures. Immobile mutagenesis sites on helix D (Q223C, K224C, and L225C) and at the kinase C-terminus (S388C, K389C) have been tested; function of proteins with these mutations is indistinguishable from wild-type. Activation loop mutations H280C, S283C, S284C, R285C, and T287C have also been tested; mutations H280C and R285C lead to severe defects in function, and mutation S283C leads to weakened binding of activator peptide TPX2.

FRET Labeling:

AurA labeling buffer consists of 20 mM HEPES pH 7.5, 300 mM NaCl, 20% glycerol. Donor fluorophore (Alexa 488 maleimide, Thermo Fisher Scientific, Waltham, Mass.) and purified AurA were incubated together at 60 μM for 2 hours at 4° C. on a rocking platform. At the end of the incubation period, samples were reduced using 10 mM DTT for approximately 15 minutes and then diluted approximately 20 fold into buffer Al (100 mM NaCl, 10% glycerol, 20 mM HEPES, pH 7.6). Samples were then purified using a HiTrap SP cation exchange column (GE Healthcare Bio-Sciences, Pittsburgh, Pa.) and eluted with a 20 column volume gradient from 0% to 100% buffer B1 (1 M NaCl, 10% glycerol, 20 mM HEPES pH 7.6). The majority singly-labeled fractions were determined using absorbance spectroscopy. Singly-labeled sample was then concentrated to approximately 50 µM using Amicon Ultra centrifuge filters (EMD Millipore, Merck KGaA, Darmstadt, Germany) and desalted into AurA labeling buffer using Zeba 7K MWCO spin columns (Thermo Fisher Scientific, Waltham, Mass.). Some donor-labeled AurA ("AurA+D") was reserved for donor-only fluorescence controls.

AurA+D was incubated at 25 µM with 100 µM acceptor fluorophore (Alexa 568 maleimide, Thermo Fisher Scientific, Waltham, Mass.) in labeling buffer for 2-8 hours. (Alexa 594 maleimide was also tested as an acceptor fluorophore, but Alexa 594-labeled samples were found to be more prone to aggregation.) After the labeling reaction, the labeled product was reduced with 10 mM DTT, centrifuged for 10 minutes at 5000 relative centrifugal force (rcf) to form pellet aggregated material, and desalted using spin columns as described above. The product, donor- and acceptor-labeled AurA ("AurA+D+A") was then quantified using UV-vis absorbance and flash frozen in single-use aliquots.

Sample quality and allosteric function was verified using mass spectrometry, kinase activity assays, and response of FRET signal to the AurA activator peptide TPX2.

Ligand Titration FRET Experiments:

The peptide TPX2 residues 1-43 (Selleck Chemicals, Houston, Tex.) was dissolved at 0.1 mM to 1.2 mM in 100 mM HEPES pH 7.5 and stored at −20° C. ADP stocks (Sigma-Aldrich Corporation, St. Louis, Mo.) were dissolved at 100 mM in 1 M HEPES pH 7.5 and stored at −20° C. Small molecule inhibitors including axitinib and MLN8054 (Selleck Chemicals, Houston, Tex.) were dissolved at 1 mM to 100 mM in DMSO and stored at −20° C.

Steady-state FRET ligand titration experiments (with ADP, TPX2, and inhibitors) were performed at room temperature at 20 nM to 50 nM AurA in ADP Quest Assay buffer +1% DMSO in a Fluoromax-4 spectrofluorometer (Horiba, Ltd., Japan). Samples were excited at 490 nm and fluorescence emission was recorded 510 nm to 750 nm.

Ligand binding data were visualized and analyzed using Microsoft Excel and Origin software. FRET was calculated using the equation E=1−(DA/D), where E is the efficiency of FRET, DA is the fluorescence of the AurA+D+A sample, and D is the fluorescence of the corresponding AurA+D control sample.

Time-resolved (TR) FRET experiments were performed using either direct waveform recording or time-correlated single photon counting (TCSPC) using instrumentation described in Muretta et al. (*Rev Sci Instrum*, 2010, 81(10): 103101). The resulting data were analyzed as described in Muretta et al. (*Proc Natl Acad Sci USA*, 2015, 112(47): 14593-8). Results obtained with both methods were similar.

Direct waveform recording experiments were performed in a 384 well plate, and measurement was performed using a NovaFluor fluorescence lifetime plate reader (Fluorescence Innovations, Inc., Minneapolis, Minn.). Details of this instrument can be found in Cornea et al. (*J Biomol Screen*, 2013, 18:97-107). Experiments were performed at 50 nM AurA in ADP Quest Assay buffer+1% DMSO. In some experiments, buffer contained no bovine γ gobulins; no change was observed in results.

TCSPC experiments were performed using a spectrometer built by the group of Dr. David D. Thomas. Details of the instrument and analysis have been previously described in Agafonov et al. (*Proc Natl Acad Sci*, 2009, 106(51): 21625-21630). Experiments were performed at 100 nM to 200 nM AurA in ADP Quest Assay buffer+1% DMSO.

Results are shown in FIG. 1 to FIG. 4.

Example 2

High-Throughput Screening Experiments:

The LOPAC1280 library (Sigma-Aldrich Corporation, St. Louis, Mo.) was evaluated for effects on the AurA FRET sensor by adding 50 µL of 20 nM AurA+D or AurA+D+A in ADP Quest assay buffer containing no bovine-γ-globulins with 1% DMSO using an Aquamax DW4 liquid dispenser (Molecular Devices, LLC, Sunnyvale, Calif.) to the each well of black Greiner 384-well plates (Sigma-Aldrich Corporation, St. Louis, Mo.) containing individual compounds from the LOPAC1280 library. These plates were then incubated for 30 minutes at room temperature (23° C.). After incubation, time-resolved fluorescence was acquired by direct waveform recording in a high-throughput nanosecond time-resolved fluorescence plate reader similar to the one described in Petersen et al. (*Rev Sci Instrum*, 2014, 85(11): 113101) or using a spectral recording plate reader, as described in Schaaf et al. (*SLAS Discovery*, 2017, 22(3): 262-273).

Two control plates were also prepared, one containing 50 microliters (µL) per well of 20 nM AurA+D and one containing 50 µL per well of AurA+D+A. Each plate contained 128 wells of apo AurA (that is, AurA without ligands), 128 wells of AurA plus 100 µM ADP, and 128 wells of AurA plus 100 µM ADP and 10 µM TPX2, all in ADP Quest buffer containing no bovine-γ-globulins with 1% DMSO. Solutions were dispensed into these plates using a multichannel pipet, and plates were incubated for 30 minutes at room temperature before acquiring time-resolved fluorescence and steady-state emission as described for the LOPAC1280 screening plates.

The time-resolved fluorescence measured in these experiments was analyzed by computing the first moment as described in Petersen et al. (*Rev Sci Instrum*, 2014, 85(11): 113101). The mean (µ) and standard deviation (σ) of the moments were calculated from AurA+D and AurA+D+A control plates. These measurements were used to calculate the Z-factor for the AurA FRET sensor with the apo samples being the negative control and the +ADP+TPX2 samples being the positive controls. In this calculation, the Z-factor was determined as described in Cornea et al. (*J Biomol Screen*, 2013, 18(1):97-107). The Z-factor using ADP+TPX2 as the positive control was >0.8.

The effect of each compound in the LOPAC1280 library on the 20 nM AurA+D or 20 nM AurA+D+A sensors was evaluated by comparing the calculated first moment from each well to the first moment of respective control plates. Hit compounds were defined as compounds in wells that exhibited first moments that were ±(5σ+µ) of the respective controls. These hits were then further analyzed and fit by various structure-based FRET models following methods described in Muretta et al. (*Proc Natl Acad Sci USA*, 2015, 112(47):14593-8).

The steady-state emission spectrum, acquired by spectral recording, was analyzed by computing the first moment of each measured emission spectra. As with the time-resolved FRET measurements acquired by direct waveform recording, the mean (µ) and standard deviation (σ) of the first moments calculated from the AurA+D and AurA+D+A control plates were used to calculate the Z-factor for the AurA FRET sensor. The Z-factor using ADP+TPX2 as the positive control was >0.8.

The effect of each compound in the LOPAC1280 library on the 20 nM AurA+D or 20 nM AurA+D+A sensors, measured by steady-state emission spectra acquired by spectral recording, was evaluated two ways: first the calculated first moment from each well was compared to the first moment of respective apo control plates and second, the value of the fluorescence intensity of the acceptor emission peak divided by the fluorescence intensity of the donor emission peak (defined as the FRET intensity ratio) was compared to the FRET ratio of the control plates. As with the time-resolved FRET analysis, hit compounds were defined as compounds in wells that exhibited first moments or FRET intensity ratio, that were ±(5σ+μ) of the respective controls. The identity of these hits was compared to the identity of hits identified by analysis of time-resolved fluorescence.

Results are shown in FIG. 5 and FIG. 6.

Example 3

Materials and Methods

Human Aurora A (AurA) Construct Expression and Purification

Constructs of human AurA (residues 122-403 plus an N-terminal poly-histidine tag separated by a TEV cleavage site) were expressed in BL21-DE3-RIL cells (Agilent Technologies, Santa Clara, Calif.). Cells were grown at 37° C. in Terrific Broth (Amresco, Solon, Ohio) supplemented with 0.5% glycerol, and protein expression was induced by the addition of 1 mM isopropyl β-D-1-thiogalactopyranoside (IPTG) at 18° C. overnight. Cells were pelleted by centrifugation at 5,000× gravity, and were resuspended in lysis buffer (50 mM Tris, pH 8.0, 500 mM NaCl, 10% glycerol, 20 mM imidazole). Cell breakage was performed on a EmulsiFlx C3 (Avestin, Inc., Ottawa, ON, Canada), and the lysate was centrifuged at 20,000 rpm for 1 hour. Protein was captured by loading lysate supernatant onto a HisTrap FF Ni-NTA column (GE Healthcare Life Sciences, Pittsburgh, Pa.), washing with lysis buffer, and eluting with elution buffer (50 mM HEPES, pH 7.5, 300 mM NaCl, 10% glycerol, 500 mM imidazole). Fractions were pooled via Bradford Assay and buffer exchanged into desalting buffer with a Desalting Column (GE Healthcare Life Sciences, Pittsburgh, Pa.). Phosphorylation states of AurA at the T288 site can be easily selected for by expressing either a C290S mutation, which disrupts autophosphorylation in *E. coli*, or a C290A mutation which favors autophosphorylation. To remove residual phosphorylation observed with the C290S construct, samples were incubated with Lambda protein phosphatase (New England BioLabs, Ipswich, Mass.) at 30° C. for 1 hour. Cation exchange was used to separate phosphorylation states. Samples were diluted ten-fold into buffer A (20 mM HEPES, pH 7.2, 50 mM NaCl, 10% glycerol) prior to loading. Diluted sample was loaded onto a HiTrap SP HP cation exchange column (GE Healthcare Life Sciences, Pittsburgh, Pa.), washed with buffer A, and eluted with buffer B (20 mM HEPES, pH 7.2, 1.0 M NaCl, 10% glycerol) in a 0% to 100% buffer B gradient over 20 column volumes. A synthetic construct of human TPX2 (residues 1-43, Selleck Chemicals, Houston, Tex.) was used in experiments that included TPX2 activation of AurA.

Labelling and Purification of FRET Probes

Site directed mutagenesis was used to incorporate cysteine residues at the L225 site of the D-helix and the S284 site of the activation loop and to remove solvent-exposed cysteine residues (C290S/A and C393S). The cysteine-lite (Cys-light) construct maintained activity in both phosphorylated and unphosphorylated states that is similar to WT AurA, as shown previously (Cyphers et al, *Nat Chem Bio*, 2016, 13:402-408.) Alexa 488 maleimide dye (Thermo Fisher Scientific, Waltham, Mass.) served as the FRET donor and was added in equimolar ratio to AurA. The reaction proceeded for 4 hours at 4° C. Singly donor labeled protein was separated by SP cation exchange, as described in Cyphers et al., and labeling with Alexa 488 was confirmed using mass spectrometry. A purified donor-only sample was set aside before labeling with FRET acceptor. Alexa 568 maleimide was used as the acceptor and was added in excess to purified donor-only protein and the reaction proceeded at 4° C. for 4 hours. Excess dye was removed by passing through a 7K MW Zeba Spin Desalting column (Thermo Fisher Scientific, Waltham, Mass.) into desalting buffer.

Kinase Inhibitor Titrations Lifetime Fluorescence Assay in 384 Well-Plate Format Commercially available Aurora kinase inhibitors were purchased from Selleck Chemicals (Houston, Tex.) and AdooQ Bioscience (Irvine, Calif.). Serial dilution of each of the inhibitors was performed to prepare 50× stock solutions in DMSO which were transferred to 96-well mother plates. Using a Mosquito HV liquid handler (TTP Labtech Ltd, UK), 1 μL of 50× stock solution was transferred from the 96-well mother plates to 384-well assay plates. After sample addition, each well in the 384-well plates contained inhibitors at final concentrations of 5000 nM, 1000 nM, 500 nM, 250 nM, 100 nM, 50 nM, 25 nM, 10 nM, 5 nM, 1 nM, or 0 nM. Each 384-well assay plate contained either four replicate titrations of 6 inhibitors or a single titration of 24 inhibitors. Donor-only and donor+acceptor labeled AurA, +/- saturating concentrations of TPX2 (either 10 μM or 20 μM), were prepared separately to a final concentration in the plates of 1 nM or 50 nM AurA in ADP Quest buffer (15 mM HEPES, pH 7.4, 20 mM NaCl, 1 mM EGTA, 0.02% Tween-20, 10 mM $MgCl_2$, 0.1 mg/mL BGG (bovine-γ-globulins), 1% DMSO). The donor-only and donor+acceptor samples were separately distributed to the 384-well assay plates using a Multidrop-Combi dispenser with standard plastic tip cassettes (Thermo Fisher Scientific, Waltham, Mass.). Plates were incubated at room temperature (25° C.) for 20 minutes prior to being read on the Fluorescence Lifetime Plate Reader which was designed and built by Fluorescence Innovations, Inc. (Minneapolis, Minn.). Instrument response function and lifetime measurements were collected as described in Gruber et al. (*J Biomol Screen*, 2014, 19(2):215-222) and Muretta et al. (*Rev Sci Instrum*, 2010, 81(10):103101).

Time-Resolved Förster Resonance Energy Transfer Data Fitting

The recorded waveforms were collected from the Fluorescence Lifetime Plate Reader and were organized in MATLAB (Mathworks, Natick, Mass.) prior to being fit on FARGOFIT (Murretta et. al, *Rev Sci Instrum*, 2010, 81(10): 103101). In MATLAB, waveforms were normalized and grouped into samples types based on the plate layout and output into a format that can be read by the fitting program. These parameters include the timescale of experiments, the instrument response function (IRF), and the matched pairs of normalized donor plus acceptor (D+A) and donor-only (D-O) waveforms for each sample. Waveforms were fit using FARGOFIT, a custom software program designed for analysis of time-resolved fluorescence (Murretta et. al, *Rev Sci Instrum*, 2010, 81(10):103101). Analysis was performed as described in Muretta, et. al. (PNAS, 2015, 112(46): 14272-14277). Briefly, the instrument response function and the model of the fluorescence decay are convolved to define the nanosecond decay which describes the measured time-resolved waveforms. The lifetime decay of the D-O is observed as a sum of exponential functions (two-exponentials are required to fit the Alexa-488 fluorescence decay). D+A samples were fit using the same exponential functions as the D-O fits, but modified by a distance-dependent FRET term, consisting of a Gaussian distribution of inter-probe distances, that describes the decrease in the lifetime relative to the D-O samples. The mean distance and full-width half maximum of the Gaussian functions were fit individually for each D+A and D-O pairing, while the parameters that described general conditions of the experiment common among all samples, such as the fraction of a given D+A sample containing D-only protein, were globally linked. Numerical fitting was performed using the Levenberg-Marquardt method.

LOPAC Library Screen

The AurA biosensor was prepared in ADP Quest buffer to a final concentration of 50 nM. D-O and D+A samples were separately distributed in 1536-well plates that had been previously plated with all compounds from the 1280 compound LOPAC library (Sigma Aldrich, St. Louis, Mo.). Plates were read on a Fluorescence Lifetime Plate Reader and direct waveforms were recorded. Plates were then read on a Spectral plate reader also designed by Fluorescence Innovations, which was used to verify screen data as well as rule out fluorescent compounds.

Results

Figure 7:
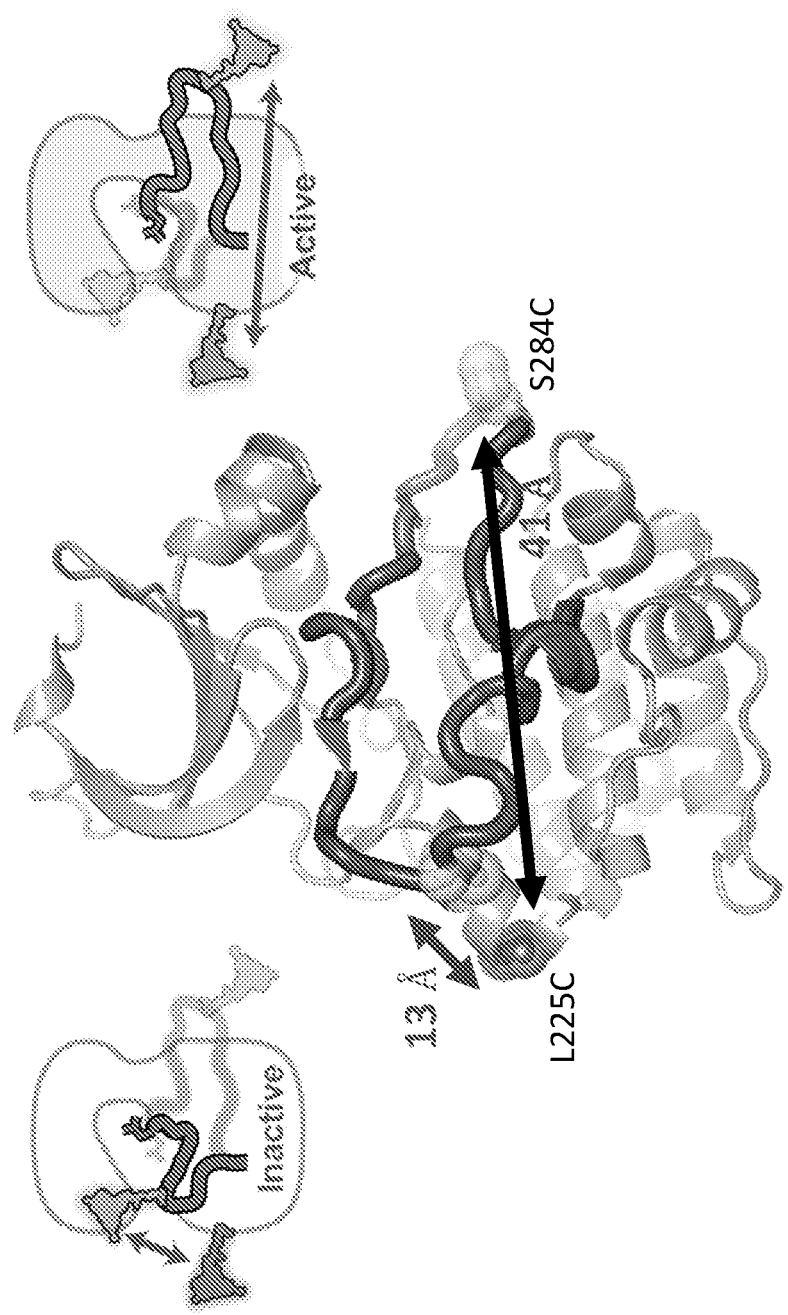
FIG. 7 shows an exemplary structural representation of an AurA Biosensor. Cysteine labeling sites added to positions L225 of the D-helix and S284 of the activation loop were labeled with a donor (Alexa 488 maleimide) and an acceptor (Alexa 568 maleimide). The amount of FRET that occurs changes in relation to the inter-dye distance between the donor and acceptor dyes. In the structures, the distances as measured from the alpha carbons of each of the labeling sites are approximately 13 Å in the DFG-Out conformation and approximately 41 Å in the DFG-In conformation. Thus, changes in FRET distances of up to 30 Å are expected when AurA converts from DFG-Out to DFG-In states.

Preparation of the AurA Biosensor—Unphosphorylated, Phosphorylated:

Time-resolved FRET (TR-FRET) was used to measure the effect of inhibitor binding on the conformation of Aurora A (AurA). To prepare the biosensor for TR-FRET measurements, cysteine labeling sites were introduced on the stationary D-helix at position L225 and on the mobile activation loop at position S284. As measured from the alpha carbons of the mutated residues, the distance between the sites in the active state is on the order of 41 angstroms, while in the inactive DFG-Out state observed in the presence of certain inhibitors, the distance is on the order of 13 angstroms (FIG. 7). These results demonstrate that up to a 30-angstrom difference can be detected from labeling at these sites. Mutagenesis of the L225 and S284 sites was performed in a cysteine-lite construct of human AurA in which the solvent exposed cysteine residues were removed to prevent non-specific labeling.

In addition to incorporating selective labeling sites for TR-FRET, it was desired that the phosphorylation state of AurA also be controllable. The addition of a C290A mutation which favors autophosphorylation at the T288 site, or the addition of a C290S mutation which inhibits autophosphorylation allows for a simple method of isolating phosphorylation states of AurA (Burgess and Bayliss, *Acta. Cryst*, 2015, 71:315-319). After phosphorylated or unphosphorylated protein was purified, the FRET donor, Alexa 488 maleimide, was conjugated to a cysteine labeling site via the maleimide reaction, and cation exchange purification was used to isolate the singly-labeled species, as confirmed by mass spectrometry. Prior to the addition of the FRET acceptor, Alexa 568 maleimide, to the remaining cysteine labeling site, donor-only labeled sample was set aside to serve as a matched donor-only control in TR-FRET experiments. Final donor-only and donor+acceptor samples +/−phosphorylation and +/−TPX2 peptide were diluted and applied to 384-well assay plates to be read in the fluorescence lifetime plate reader (Fluorescence Innovations, Inc., Minneapolis, Minn.).

6-Inhibitor Plates—FRET Distance Determinations—DMSO Controls

Figures 8A, 8B, 8C:
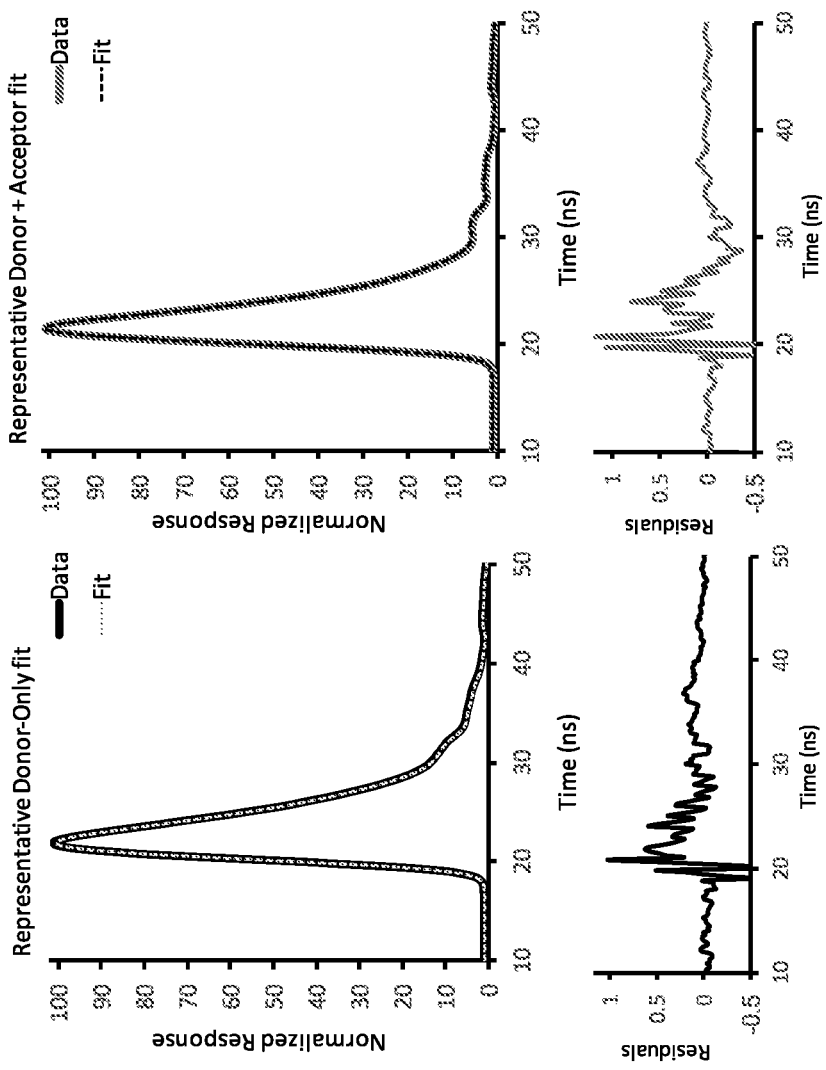
FIG. 8A. The decrease in donor lifetime in the presence of the acceptor, as described by FRET, is evident when the donor-only and donor+acceptor samples are plotted together. Using a custom program designed for time-resolved FRET (TR-FRET) analysis, normalized waveforms were fit to a model which describes the decrease in lifetime in the donor+acceptor sample relative to the donor-only sample in the form of a distance-dependent energy transfer term. Final fits of donor-only samples (FIG. 8B) and donor+acceptor samples (FIG. 8C) are shown, with residuals less than 1.0% of the data.

Fluorescence lifetime measurements were performed in 384-well plates using the Fluorescense Lifetime Plate Reader built by Fluorescence Innovations (Minneapolis, Minn.) based on direct waveform recording technology and previously described (Peterson et al., *Rev. Sci. Instrum.*, 2014, 85(11):113-101). Representative fluorescence lifetime waveforms are shown in FIG. 8A. To extract measurements of inter-dye distance from the fluorescence lifetime data, donor-only (D-O) and donor+acceptor (D+A) pairs of waveforms were fit to a single Gaussian inter-probe distance distribution function using FARGOFIT (Murretta et. al, *Rev Sci Instrum*, 2010, 19(2): 215-222). Donor-only fluorescence waveforms (FIG. 8B) were modeled using a multiexponential decay function, which accounts for the intrinsic lifetimes of Alexa 488. The donor+acceptor waveform (FIG. 8C) was modeled from the amplitudes and lifetimes present in the matched donor-only sample and modified so that a distance-dependent resonance energy transfer term describes the decrease in fluorescence lifetime relative to the donor-only control. An iterative fitting procedure was employed in which parameters that could be shared across the plate were initially globally constrained while the remaining parameters settled into photo-physically realistic values, and then released to finalize the distance determinations. In the final iteration, the distance and full-width half maximum of the Gaussian model were allowed to vary individually for each sample. The residuals from the final fits are determined to less than one percent of the data, shown in FIG. 8B and FIG. 8C, and demonstrate the robustness of the fits.

Figure 9A:
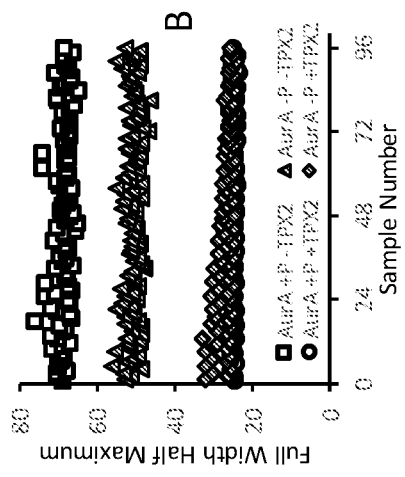
FIG. 9A. DMSO samples from each 384-well assay plate (96 per plate) were fit to the single Gaussian distance distribution model, as described in Example 3. Final interprobe distance determinations for each control sample are displayed. The standard deviations of each set of 96 replicates are less than 1 Å. Phosphorylated and unphosphorylated AurA yield inter-probe distances of approximately 30 Å in the absence of TPX2 and are indistinguishable from each other by distance alone. Unphosphorylated AurA exhibited an inter-probe distance of approximately 50 Å in the presence of TPX, consistent with a conformational shift of approximately 20 Å in response to the addition of TPX2. Phosphorylated AurA plus TPX2 can be distinguished from unphosphorylated AurA plus TPX2 by a further increase in the distance of about 5 Å. The grouping of the phosphorylated AurA+TPX2 data points into pairs of slightly higher and slightly lower values can be explained by plate effects during sample distribution and data collection and was not observed in any other plate in this dataset.
Figure 9B:
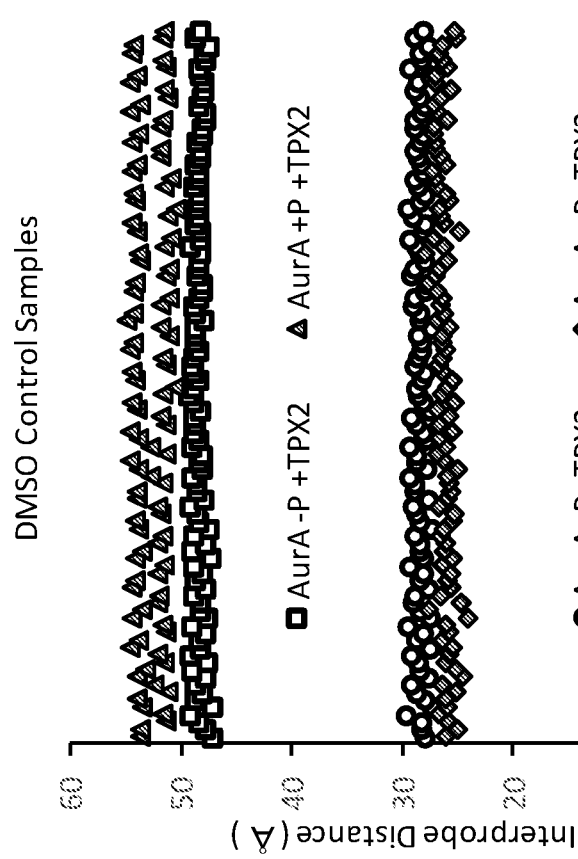
FIG. 9B. The Gaussian full-width half-maximum values show that there is a wider distribution of distances in the samples without TPX2, and narrower distributions in the samples with TPX2.

To model the structural states of AurA in the absence of inhibitors, 96 DMSO control replicates for each of the four biochemical states of AurA (unphosphorylated +/−TPX2 and phosphorylated +/−TPX2) were fit as described above. During this fitting procedure, the fraction of the donor+acceptor samples that lacked acceptor dye were determined globally for individual protein preparations (that is, separately for unphosphorylated C290S AurA +/−TPX2 and for phosphorylated C290A AurA +/−TPX2). The final distance determinations for DMSO control samples from each of the four biochemical states are shown in FIG. 9A. For each biochemical state, the errors in the distance determinations, as reflected by the standard deviation across all 96 replicates, were on the order of +/−1 Angstrom.

Figure 9C:
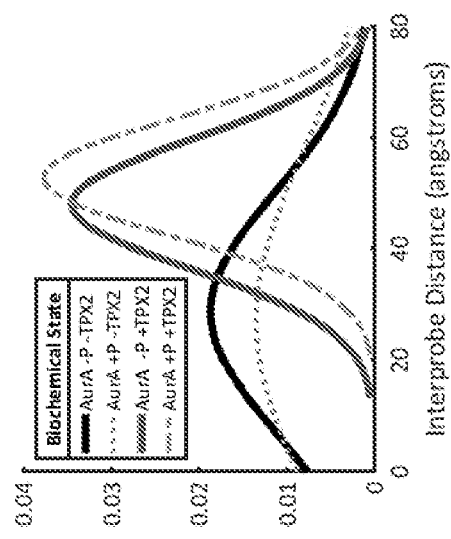
FIG. 9C. Representative plots of the Gaussian distance distributions derived for each biochemical state, highlighting the shifts to longer distance and the narrowing of the distributions observed in the presence of Tpx2.

These data reveal a clear trend in which the inter-dye distance for both the unphosphorylated and phosphorylated samples changes from approximately 30 Å in the absence of TPX2 to approximately 50 Å in the presence of TPX2, indicating a switch to the active DFG-In conformation of the kinase. In addition, a large full width at half maximum was observed in the absence of TPX2 (FIG. 9B), indicating a broad distribution of structural states. In contrast, the distance distributions were observed to narrow significantly in the presence of TPX2, suggesting that the structure of the kinase becomes considerably more homogeneous when TPX2 is present. This is further demonstrated by plotting representative Gaussians distance distributions for each of the four biochemical states (FIG. 9C). These results are consistent with prior observations of AurA made by infrared spectroscopy that demonstrated that TPX2 triggers a conformational change from the DFG-Out to the DFG-In state (Cyphers et al, *Nat Chem Bio,* 2016, 13: 402-408).

A small but statistically significant difference was also observed between the unphosphorylated and phosphorylated samples in the presence of TPX2, with the phosphorylated sample yielding a longer distance of 52 angstroms, and the unphosphorylated sample a shorter distance of 48 angstroms. This difference may be due to phosphorylation further constraining the the activation loop in the active DFG-In state.

Interestingly, phosphorylation alone (without TPX2) does not result in a substantial change in the measured inter-dye distance compared with the unphosphorylated kinase. This result indicates that TPX2 is still required to switch AurA to the DFG-In state even when the kinase is phosphorylated.

6-Inhibitor Plates—FRET Distance Determinations—Inhibitors

The waveforms measured in the presence of a maximal concentration (5 µM) of each inhibitor were fit as described above. For each inhibitor, a DMSO control was included in the fitting as an internal standard (FIG. 10A). For the samples lacking TPX2, the inhibitors were observed to cluster into two groups exhibiting either long (45 Å to 49 Å) or short inter-probe distances (22 Å to 30 Å) (FIG. 10B). These measurements indicate that three of the inhibitors induce the DFG-In state when they bind to AurA (PHA-680632, SNS-314, and TAE-684), while three of the inhibitors bind to the DFG-Out state of the kinase (Danusertib, MLN-8054, VX-680). These results agree nicely with X-ray structures of AurA bound to Danusertib (FIG. 11A) and MLN-8054 (FIG. 11B), in which AurA adopts the DFG-Out state, and AurA bound to SNS-314 (FIG. 5C) in which the kinase adopts the DFG-In state.

Interestingly, the presence of TPX2 completely altered the observed pattern of inhibitor-induced distances (FIG. 10B). When the phosphorylated kinase was bound to TPX2, fitting of the data for all 6 inhibitors revealed distances that were consistent with the DMSO control experiments (approximately 50 Å), and with the kinase adopting the DFG-In state. These results indicate that any conformational preference of the three DFG-Out compounds Danusertib, MLN-8054, and VX-680, for the DFG-Out state of AurA is sufficiently small to be counteracted by the action of TPX2. In the case of VX-680, this result is confirmed by the crystal structure of VX-680 bound to the AurA:TPX2 complex, which shows the kinase in the DFG-In state (Zhao et al., *Protein Sci,* 2008, 17(10): 1791-1797). However, for the unphosphorylated samples bound to TPX2, the distinction between the DFG-Out and DFG-In compounds was still apparent in the form of slightly shorter distances for the DFG-Out compounds (Danusertib, MLN-8054 and VX-680) that were intermediate in value between the distances observed in the absence of TPX2, and the distances observed in the presence of both TPX2 and phosphorylation (FIG. 10B). This result suggests that under these conditions the opposing effects of TPX2 and the DFG-Out compounds result in a conformational equilibrium between DFG-Out and DFG-In states. This interpretation is consistent with published work showing that TPX2 has a relatively modest effect on the DFG equilibrium (Cyphers et al. *Nat Chem Bio,* 2016, 13: 402-408). These data also demonstrate that the TR-FRET method described herein has the capability to distinguish between compounds that promote a homogeneous structural state and compounds that induce a conformational equilibrium.

Figure 12C:
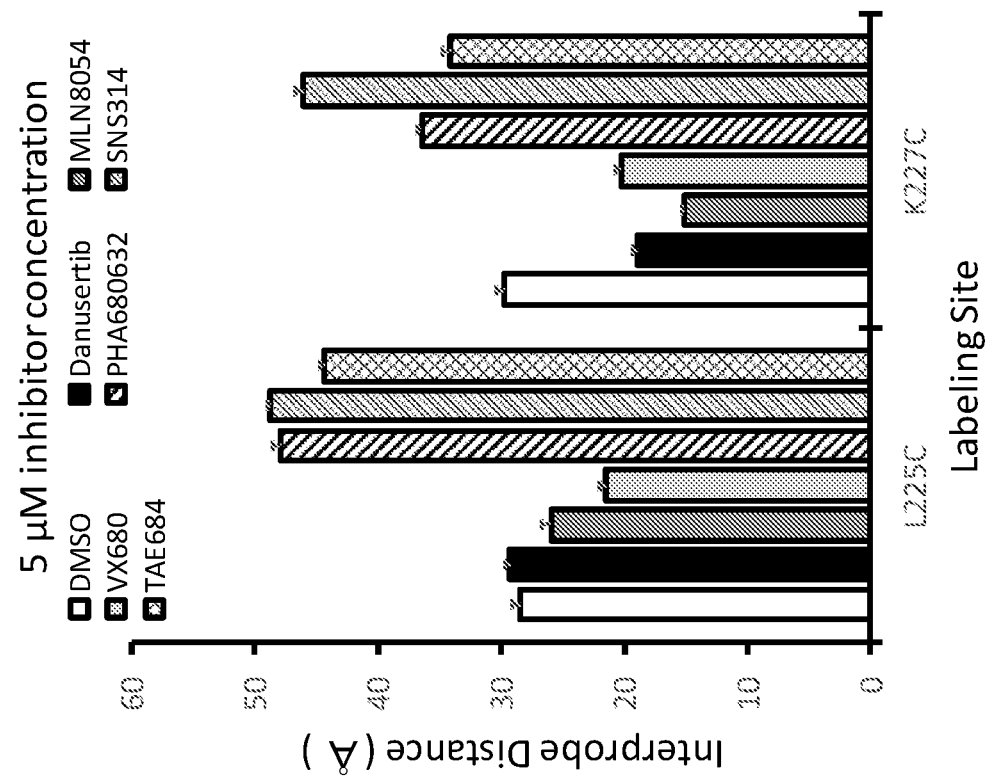
FIG. 12C. Distances obtained in the presence of the six inhibitors are shown for the two sets of labeling sites. Values are the means and standard deviations from four replicate measurements of each compound. Very similar results were obtained with the two sets of labeling sites, confirming the robustness of the DFG-In/Out assignments obtained by FRET.
Figure 12A:
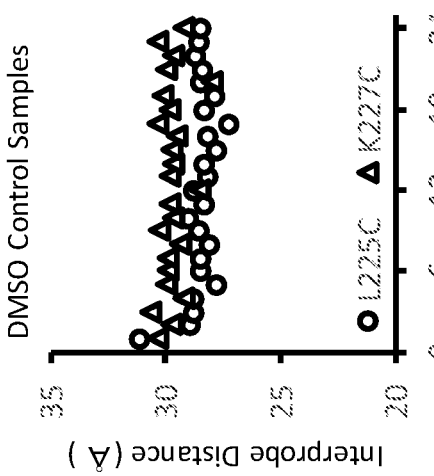
FIG. 12A and FIG. 12B. Analysis of the DMSO controls revealed that the measured interprobe distances (FIG. 12A) and widths (FIG. 12B) are similar for the samples labeled at the L225 versus K227 sites.
Figure 12B:
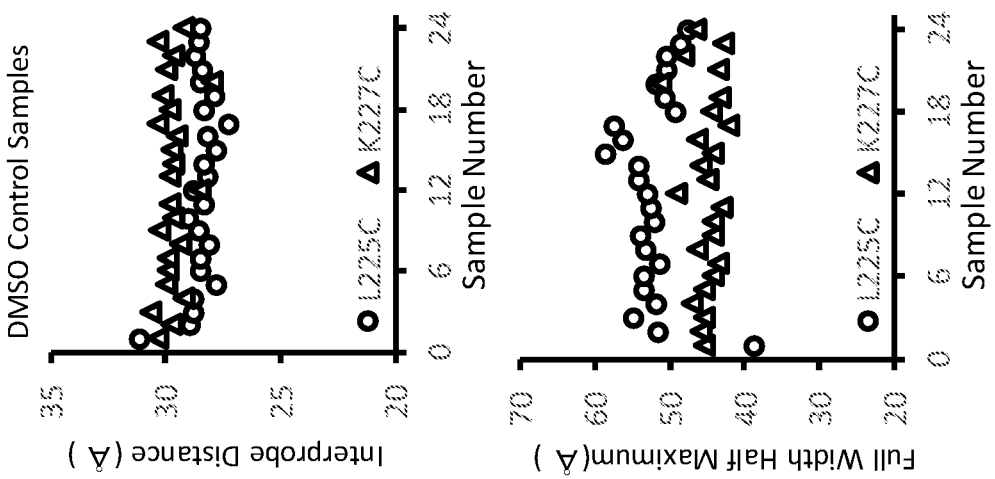

To demonstrate that the patterns observed in the above results are general and not the sole outcome of the specific choice of labeling sites, a new kinase biosensor construct was created where the fluorescent dye on the D-helix was moved from L225 downstream to position K227, and the inhibitor binding experiments were repeated with this new sensor containing dyes at K227C and S284C. Fitting the waveforms as described above for the DMSO control samples revealed that the distances (FIG. 12A) and full width half-maxima values (FIG. 12B) measured with this new biosensor were very similar to those obtained previously with the old sensor labeled at the L225C and S284C sites. Additionally, the new biosensor yielded very similar results to the previous biosensor when bound to the 6 inhibitors, confirming the DFG-In/DFG-Out assignments of the compounds (FIG. 12C).

1280 Compound LOPAC Library Screen

Traditional kinase inhibitors bind to the ATP-binding site of the kinase and are thus competitive with ATP binding. These types of compounds induce conformational changes by direct binding interactions with the kinase DFG-motif. With the inhibitor titration plates, the ability of a kinase to model the conformation of known ATP competitive binding compounds and the structural states that they prefer has been demonstrated. To demonstrate the ability of the AurA biosensor to detect not only ATP-competitive compounds but also compounds that bind to other allosteric sites on the kinase and modify conformation or modulate kinase activity, a novel screening strategy was devised. First, a duplicate screen of the AurA biosensor against the LOPAC library was run in a 1536-well plate format. Donor-only as well as donor+acceptor samples were run so that distance determinations could be made of identified hits, if desired.

Direct-recorded waveforms were fit to a single exponential model of decay by using the least-squares minimization global analysis software designed by Fluorescence Innovations to determine a fluorescence lifetime for each of the wells. (Gruber et al. *J Biomol Screen,* 2015, 19(2): 215-222). Donor+acceptor waveforms were used to determine hits because of the large changes in lifetimes from FRET that are likely to be present upon compound binding. Hits were revealed by calculating the average lifetime of the 256 DMSO samples (FIG. 13A) that were present in each plate and then defining hits as a change in lifetime by 5 standard deviations (SD) about the mean of the controls. Fluorescent compounds were ruled out using the spectral similarity index in which false positives are ruled out by 3 SD of the mean of controls. Plotting the donor+acceptor lifetimes measured in the two replicate plates revealed a high degree of consistency between the replicate screens and demonstrated the robustness of these data (FIG. 13B). Furthermore, the analysis revealed many hits in agreement between screen replicates (72 hits in common).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method comprising:
    providing a protein kinase comprising a donor molecule, an acceptor molecule, and a protein kinase domain;
        wherein the donor molecule or the acceptor molecule or both the donor molecule and the acceptor molecule comprise a dye;
        wherein the donor molecule and the acceptor molecule are covalently linked to the protein kinase;
        wherein the donor molecule or the acceptor molecule or both are covalently linked to the activation loop, the alpha-C helix, the D-helix, or the phosphate binding P-loop of the protein kinase domain;
        wherein the protein kinase can exist in at least a first conformation and a second conformation;
        wherein in the first conformation, energy is transferred from the donor molecule to the acceptor molecule;
        wherein in the second conformation, the efficiency with which energy is transferred from the donor molecule to the acceptor molecule differs from the efficiency with which energy is transferred from the donor molecule to the acceptor molecule in the first conformation; and
    measuring the proportion of protein kinase in the first conformation and measuring the proportion of protein kinase in the second conformation;
        wherein a conformational change from the first conformation to the second confirmation indicates allosteric activation or allosteric inhibition of the kinase, and wherein the conformational change is a nanometer-scale distance;
        wherein measuring the proportion of protein kinase in a conformation comprises measuring Förster resonance energy transfer (FRET) from the donor molecule to the acceptor molecule; and
        wherein measuring FRET comprises acquiring a steady-state FRET measurement, or a time-resolved FRET measurement, or both.

2. The method of claim 1, wherein when the kinase is in the second conformation, the distance between the donor molecule and the acceptor molecule differs by at least 1 Angstrom (Å) from the distance between the donor molecule and the acceptor molecule when the protein kinase is in the first conformation.

3. The method of claim 1,
    wherein the protein kinase can exist in a third conformation,
    wherein when the kinase is in the third conformation, the efficiency with which energy is transferred from the donor molecule to the acceptor molecule differs from the efficiency with which energy is transferred from the donor molecule to the acceptor molecule in the first conformation and differs from the efficiency with which energy is transferred from the donor molecule to the acceptor molecule in the second conformation, and
    wherein the method further comprises measuring the proportion of protein kinase in the third conformation.

4. The method of claim 3, wherein when the kinase is in the third conformation, the distance between the donor molecule and the acceptor molecule differs by at least 1 Angstrom (Å) from the distance between the donor molecule and the acceptor molecule when the protein kinase is in the first conformation and differs by at least 1 Å from the distance between the donor molecule and the acceptor molecule when the protein kinase is in the second conformation.

5. The method of claim 1, wherein the method further comprises exposing the protein kinase to a nucleotide, an activator protein, an activator peptide, or a small-molecule allosteric modulator, or a combination thereof.

6. The method of claim 1, further comprising
    providing a small molecule;
    contacting the protein kinase with the small molecule; and
    determining the proportion of a first conformation adopted by the protein kinase when the small molecule is in contact with the protein kinase.

7. The method of claim 1,
    wherein the donor molecule is covalently linked to the activation loop of the protein kinase;
    wherein the donor molecule is covalently linked to the kinase domain C-helix of the protein kinase;
    wherein the donor molecule is covalently linked to the kinase domain D-helix of the protein kinase; or
    wherein the donor molecule is covalently linked to the phosphate binding P-loop of the protein kinase.

8. The method of claim 1, wherein
    the donor molecule is covalently linked to the activation loop and the acceptor molecule is covalently linked to the D-helix, or
    the acceptor molecule is covalently linked to the activation loop and the donor molecule is covalently linked to the D-helix.

9. The method of claim 1, wherein the donor molecule or the acceptor molecule are covalently linked to the activation loop.

* * * * *